United States Patent [19]
McGrady et al.

[11] Patent Number: 5,848,593
[45] Date of Patent: Dec. 15, 1998

[54] SYSTEM FOR DISPENSING A KIT OF ASSOCIATED MEDICAL ITEMS

[75] Inventors: R. Michael McGrady, Baden; Sean M. McCune, Natrona Heights, both of Pa.

[73] Assignee: Diebold, Incorporated, North Canton, Ohio

[21] Appl. No.: 756,623

[22] Filed: Nov. 26, 1996

Related U.S. Application Data

[63] Continuation-in-part of Ser. No. 361,783, Dec. 16, 1994.

[51] Int. Cl.$^6$ .................................................. G08B 13/24
[52] U.S. Cl. ................................ 128/897; 221/1; 221/5; 340/568
[58] Field of Search .................................. 128/897, 898; 221/1, 2, 15, 5, 94; 364/413; 395/228; 340/572, 825, 568; 235/385; 705/28

[56] References Cited

U.S. PATENT DOCUMENTS

| | | | |
|---|---|---|---|
| 3,752,359 | 8/1973 | Shaw | 221/5 |
| 4,695,954 | 9/1987 | Rose et al. | 364/413 |
| 4,839,806 | 6/1989 | Goldfischer et al. | 364/413 |
| 4,926,885 | 5/1990 | Hinkle | 128/898 |
| 5,260,690 | 11/1993 | Mann et al. | 340/572 |
| 5,303,844 | 4/1994 | Muehlberger | 221/1 |
| 5,377,864 | 1/1995 | Blechl et al. | 221/2 |
| 5,431,299 | 7/1995 | Brewer et al. | 221/2 |
| 5,448,226 | 9/1995 | Failing, Jr. et al. | 340/825.35 |
| 5,455,409 | 10/1995 | Smith et al. | 235/385 |
| 5,671,362 | 9/1997 | Cowe et al. | 395/228 |

*Primary Examiner*—John G. Weiss
*Assistant Examiner*—V. Srivastava
*Attorney, Agent, or Firm*—Ralph E. Jocke

[57] ABSTRACT

A system for monitoring and dispensing medical items, includes a data terminal (76) which is connected through a local area network (82) to at least one remote computer (84) including a processor and the data store. The data store includes data representative of medical items which may be stored in dispensing devices (96, 100) or in storage locations external to said dispensing devices. The data store further includes data representative of information concerning patients. The data store further includes information concerning kits which kits include more than one of the available medical items. The items in each kit are used in the course of a medical procedure. A user is enabled to interface with the data terminal to select a patient and a kit for use by the patient. A user is further enabled to dispense items included in a selected kit, and data representative of the taking of the items in the kit for use by the patient is stored in correlated relation with the information concerning the patient in the data store.

29 Claims, 30 Drawing Sheets

Side View

FIG. 29

Patient Info Window:

Patient Information - (Edith, Jennifer (203) Room: ER, Bed: P1) — 236

Patient ID: 203
Med Rec #: 06

Patient Name: Edith, Jennifer J.
Sex: F
Height: 3.10
Weight: 95 lbs
Date of Birth: 2/25/79

Admitted
Date: 8/20/96
Time:

Location
Room: ER
Bed: P1

Physician: Doctor MD., Dr. Emil Richard
Allergies: Penicillin/Cephalosporin

Help — 240
Close — 238

FIG. 30

Patient Usage Browser:

Patient Usage Browser - (Edith, Jennifer (203) Room: ER, Bed: P1)

| Date/Time | Status | Generic Name | Qty | Size |
|---|---|---|---|---|
| 20-Aug 07:35 | Taken | Tetanus & Diptheria Toxoids | 1 | 0.5ml |
| 20-Aug 06:02 | Taken | Alprazolam | 1 | 0.25mg |
| 20-Aug 06:02 | Taken | Erythromycin | 1 | 28tablets |
| 20-Aug 06:01 | Taken | Albuterol | 1 | 17gram |
| 20-Aug 04:45 | Taken | Diphenhydramine | 1 | 50mg |
| 20-Aug 04:45 | Taken | Dexamethasone | 1 | 4mg |

[Trade Name] [Discrepancy] [Return] [Help]

[Prev Page] [Waste] [Close]
[Next Page]

FIG. 31

Med Order Window:

MedOrder Browser - ( Miller, Robert (303) Room: 3North, Bed: 310A )

| Generic Name<br>Route | CR | Order<br>Freq | Qty | Ordered Dose<br>Unit Dose | Start Time<br>End Time | Review<br>Check |
|---|---|---|---|---|---|---|
| Warfarin<br>Oral | | 222920<br>q6pm | 1 | 7.5 mg<br>7.5 mg | 08/18/96 00:00 | C |
| Prochlorperazine<br>Intramuscular | | 222900<br>q8hpm | 1 | 10 mg<br>10 mg | 08/15/96 00:00 | C |
| Ibuprofen<br>Oral | | 222934<br>qidpm | 1 | 800 mg<br>800 mg | 08/20/96 00:00 | C |
| Lisinopril<br>Oral | | 222899<br>qam | 2 | 15 mg<br>10 mg | 08/15/96 00:00 | R |
| Allopurinol<br>Oral | | 222933<br>qam | 1 | 300 mg<br>300 mg | 08/20/96 00:00 | C |

[Prev Page] [Next Page] [Trade Name] [Info] [Dispense] [Help] [Close]

FIG. 32

Supply Browser:

| Generic Name | Size | Strength | Qty | CR |
|---|---|---|---|---|
| Morphine | 10mg | 10mg/1ml | 1 | * |
| Naloxone | 0.4mg | 0.4mg/1ml | | |
| Nifedipine | 10mg | 10 mg | | |
| Nifedipine | 30mg | 30 mg | | |
| Nitroglycerine | 50mg | 50mg/500ml | | |
| Omeprazole | 20mg | 20mg | | |
| Oxycodone/Acetaminophen | 5/325mg/ | 5/325mg | | |
| Prednisone | 5mg | 5 mg | | |
| Prochlorperazine | 10mg | 10mg/2ml | | |
| promethazine | 25mg | 25mg/1ml | | |

Supply Browser - (Edith, Jennifer (203) Room: ER, Bed: P1)

Select Quantity
1, 2, 3, 4, 5, 6, 7, 8, 9, 10

Buttons: Trade Name, Phys/Route/Site, Info, Dispense, Help, Close, Prev Page, Next Page

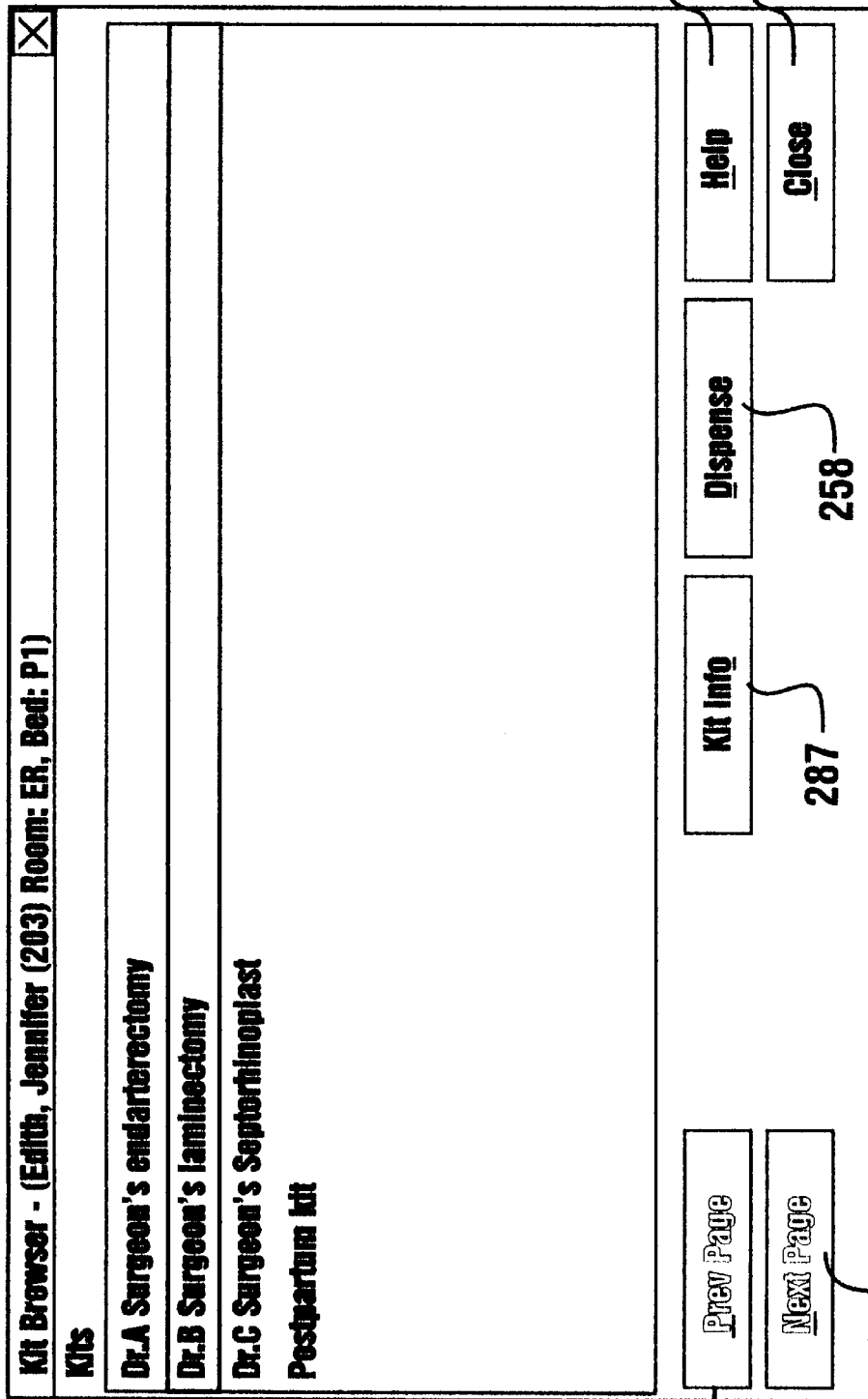

FIG. 34

Kit Info Window:

Kit Information - (Edith, Jennifer (203) Room: ER, Bed: P1)
Kit Dr.B Surgeon's laminectomy

| Generic Name | Size | Strength | Kit Qty | DT Qty | CR |
|---|---|---|---|---|---|
| Bacitracin | 50,00 | 50,000 un | 1 | 13 | |
| Gelfoam sponge | 1 spon | large | 1 | 9 | |
| Lidocaine w/ Epinephrine | 30ml | 1% 30ml | 1 | 0 | |
| Methylprednisolone Sodium Succinate | 125m | 125mg/2 | 1 | 0 | |
| Thrombin, topical | 1000u | 1000 unit | 1 | 9 | |

Trade Name — 252

Prev Page / Next Page — 224, 226

Help — 240
Close — 238

Supply Browser - (Shakespeare, William (0120002) Room: KDCUBE, Bed: 2)

| Generic Name | Size | Strength | Qty | CR | Select Quantity |
|---|---|---|---|---|---|
| BRETYLIUM | 1AMP | 500MG A | | | 1 |
| | | | | | 2 |
| | | | | | 3 |
| | | | | | 4 |
| | | | | | 5 |
| | | | | | 6 |
| | | | | | 7 |
| | | | | | 8 |
| | | | | | 9 |
| | | | | | 10 |

Prev Page | Trade Name | Info | Dispense | Help
Next Page | Phys/Route/Site | | | Close 252 — Trade Name

Supply Browser - (Shakespeare, William (0120002) Room: KDCUBE, Bed: 2)

| Generic Name | Size | Strength | Qty | CR |
|---|---|---|---|---|
| BRETYLOL | 1AMP | 500MG A | | |

Select Quantity
- 1
- 2
- 3
- 4
- 5
- 6
- 7
- 8
- 9
- 10

252 — Generic Name

Phys/Route/Site

Prev Page | Info | Dispense | Help
Next Page | | | Close

SYSTEM FOR DISPENSING A KIT OF ASSOCIATED MEDICAL ITEMS

This application is a continuation in part of application Ser. No. 08/361,783 filed Dec. 16, 1994.

TECHNICAL FIELD

This invention relates to medical inventory monitoring and dispensing devices and systems. Particularly this invention relates to apparatus for dispensing and tracking an inventory of medical items used to treat patients in a hospital, clinic or other healthcare setting.

BACKGROUND ART

The treatment of patients in hospitals and clinics usually involves the receipt by the patient of medical items. These items may include consumable items such as medications. Medical treatment may also involve other disposable items such as dressings and bandages or other medical equipment. Items implanted into the patient or used in conjunction with surgical procedures may also be used and consumed during the course of a patient's medical treatment. Examples of such items include splints, catheters or guide wires which are normally used during cardiac catheterization or angioplasty. To serve the needs of its patients, a clinic or hospital must always maintain sufficient stocks of these items on hand. Further, as medical items are often expensive, the charges associated with their use must be accurately billed to the patient.

Currently most systems for tracking inventory and use of medical equipment items in a hospital or clinic environment are manual systems. The persons responsible for maintaining an inventory of particular items must monitor the use of the items in each storage location within the hospital and order additional supplies when it is noted that the available stocks are running low. Often personnel are only familiar with the stocks available in a particular storage location and as a result, additional stocks may be ordered even though ample supplies are available elsewhere in the same facility.

Certain drugs used in the course of medical treatment are regulated narcotics. Supplies of such drugs must be kept in secure cabinets. Items may be dispensed from the secure cabinets only by two (2) authorized users accessing the material and certifying the manner in which it is used. The use of such narcotics also may require considerable paperwork which takes away valuable time that could be used for treating patients.

The recording of medical items so that the patient may be billed for their use in the course of treatment is also largely a manual operation. The fact of use by the patient must be recorded in the patient's chart for later billing. In some cases items have peel-off labels that include a bar code that can be scanned and used for billing purposes. However, this still requires that the nurse or medical technician transfer the correct coding to the proper location for later billing.

Complications in billing become even greater when items are removed from inventory to accomplish a planned surgical procedure and then the items are not used. A patient may be charged for use of a particular item which is removed from inventory in anticipation of surgery. If during the surgery the item is not needed, a corresponding credit must be issued when the item is returned to stock. All of these activities take time away from persons who could otherwise devote their time to the treatment of patients. Such tracking and billing practices are also prone to inaccuracies which may cause the hospital or clinic to lose money or which may result in overbilling of the patient.

Thus there exists a need for an apparatus and system for monitoring and dispensing medical items in hospital or clinic environments that can more accurately monitor inventories, dispense medical items and correlate the use of medical items with the patient whose treatment has included their use.

DISCLOSURE OF INVENTION

It is an object of the present invention to provide a system for monitoring an inventory of medical use items to provide an indication of what items have been used.

It is a further object of the present invention to provide a system for monitoring the use of medical use items so that supplies may be replenished before depletion.

It is a further object of the present invention to provide a system for monitoring an inventory of medical use items that monitors a plurality of items in real time.

It is a further object of the present invention to provide a system for monitoring an inventory of medical use items that requires the processing of no paper forms.

It is a further object of the present invention to provide a system for monitoring and dispensing medical use items that indicates the patient whose treatment has involved the medical use items.

It is a further object of the present invention to provide a system for monitoring and dispensing medical use items that can be used to indicate the technician or physician who has used such medical use items.

It is a further object of the present invention to provide a system for monitoring and dispensing medical use items that provides for crediting of a patient's account upon return of an unused item to inventory.

It is a further object of the present invention to provide a system for monitoring and dispensing medical use items that is used to store and dispense restricted items in a secure manner.

It is a further object of the present invention to provide a system for monitoring and dispensing medical use items that can guide a user to select the items that will be used in a particular medical procedure.

It is a further object of the present invention to provide a system for monitoring and dispensing medical use items that may be used to track and dispense a wide variety of various items and to record their use in a clinical or hospital environment.

It is a further object of the present invention to provide a system for monitoring and dispensing medical use items that enables a user in the course of a dispensing sequence to selectively review and dispense medications by either the generic name or the brand name.

It is a further object of the present invention to provide a system for monitoring and dispensing medications that enables a user to dispense together predetermined medical items that are used as a kit in the conduct of a medical procedure.

It is a further object of the present invention to provide a dispensing mechanism that reliably dispenses medicines to a user in response to the user's selection of items.

Further objects of the present invention will be made apparent in the following Best Modes for Carrying Out Invention and the appended claims.

The foregoing objects are accomplished in a preferred embodiment of the invention by a system for monitoring and dispensing medical items in a clinical or hospital environment. This system includes a plurality of item storage locations. A particular type of medical item may be stored in each location. For example, one type of medical item may include a particular type of catheter. Another may be a particular type of medication packaged in a particular dosage. Each location in the system includes at least one unit of the particular type of medical item.

A sensor is positioned adjacent to each location. A sensor is particularly adapted to sense the addition or subtraction of a unit of the particular type of medical item that is stored in the location. As a result, each time a unit of the particular item is added or removed from storage in the location, the sensor senses this and generates a signal.

A counter is connected to each sensor and records the number of units added or removed from each location. The counter holds a count of the change in the number of units at the location since the last time the counter was read.

The counters associated with each location are connected to at least one processor and at least one memory or data store. The data store includes a total of the number of items that are located in storage at the location. Periodically, the processor polls each of the counters and reads the change in the number of units stored therein. Thereafter the processor is operative to update the total number stored in the memory to reflect the number of items currently stored at the location.

Embodiments of the invention include a data terminal which includes a user interface and which terminal is connected to the processing system and the counters. The data store includes records concerning patients, procedures, authorized users of the system and each of the products stored in each of the locations, including pricing information. The data store further includes data in correlated relation concerning the brand names and generic names for medications and other medical items stored in the locations of the system. The data store further includes information on "kits" which are groups of medical items that are used together. Such kits may be groups of items which are used together repeatedly, such as in doing a diagnostic test. Alternatively, a kit may comprise items that are to be used on a one-time basis, such as for a particular patient's operative procedure. The data on items in each kit are stored in correlated relation with the kit designation in the database.

The user, such as a technician or nurse, uses the interface of the data terminal to identify the particular patient who is to receive the medical items taken by the user. Upon removal or dispense of the items from the storage locations, the use of such items is recorded in the patient record in the data store so that the patient's chart may be automatically updated and the item charged. In addition, a user using the data terminal may review information in the data store concerning procedures and physicians to determine what medical items are required by a physician to conduct a procedure and may remove such items for delivery to an operating room. This information may include kits which relate to particular procedures. The user is enabled to take or cause medical items to be dispensed through input to the data terminal.

The user may also use the interface of the data terminal to check stocks of medications which are available as well as medications which have been prescribed for a patient. The user is enabled to use the interface to check the brand name for medical items designated by generic name, and vice versa. This is done by the user interface interfacing with the drug information stored in the data store. This enables a user to check for the availability of medications by either brand or generic name. This also enables a user to check the appropriate character of an item prescribed by checking its other name. This also enables a user to determine the availability and use a brand name or generic name equivalent to the medical item prescribed, when the brand or generic type prescribed is not available.

In embodiments of the invention, controlled substances such as narcotics, may be dispensed using the system from a dispenser mechanism or an electronic lock drawer. In such embodiments, the user is required to identify himself at the display terminal. This information is processed and compared to authorized user records in the data store to verify that the user is an authorized user. In some embodiments the identifying information on the user may be placed on an encoded object such as a card and the user may be assigned a personal identification number (PIN) that is memorized by the user. The data terminal includes a reader for reading the coded object and for receiving the user's PIN number which has a predetermined relationship to the data on the encoded object. The proper input of the PIN with the corresponding user's coded object verifies that a proper user is requesting to gain access to the items. For some strictly controlled substances two (2) authorized users may be required to input their coded objects and PIN numbers in order to gain access to the controlled items.

As with the previously described embodiment, once the authorized user has provided the necessary identification, the processor operates to cause the desired substance to be dispensed or made accessible to the user. The user is also required to input the corresponding patient data so that the patient's chart and billing may be updated.

In embodiments of the invention, the system may interface with other computer systems such as the admission-discharge-transfer (ADT) computer system that the hospital uses to track patients. This is a computer system which is used in a hospital or clinic to track patient location and activity. In addition, the system of the present invention may also be connected to the hospital information system (HIS) which is the record storage facility of the hospital which maintains computerized records concerning patients. The system may be interfaced to the pharmacy system which keeps records of medications prescribed for each patient. As a result, patient activity, record keeping, and billing may be automated through the system of the present invention, along with inventory monitoring. The system of the present invention may also be used to produce a wide variety of reports from the data store related to patients, authorized users, physicians and various types of items used in inventory. Such a system may also be integrated with an automatic ordering system so as to transfer supplies from one location to another where they are needed and/or to automatically place orders for additional supplies with vendors when supply levels reach a limit.

BRIEF DESCRIPTION OF DRAWINGS

FIGS. 28 through 37 are windows displayed on the touch screen of the data terminal in a preferred embodiment of the invention, with FIG. 28 being a patient browser window.

FIG. 29 is a patient information window.

FIG. 30 is a patient usage browser window.

FIG. 31 is a med order browser window.

FIG. 32 is a supply browser window.

FIG. 33 is a kit browser window.

FIG. 34 is a kit information window.

FIG. 35 is a supply browser window selected to display trade name information for the displayed medical items.

FIG. 36 is a supply browser window like FIG. 35 selected to display generic name information for the displayed medical items.

FIG. 37 is a physician/route/site browser window selected to display route information for a medication.

BEST MODES FOR CARRYING OUT INVENTION

Figure 1:
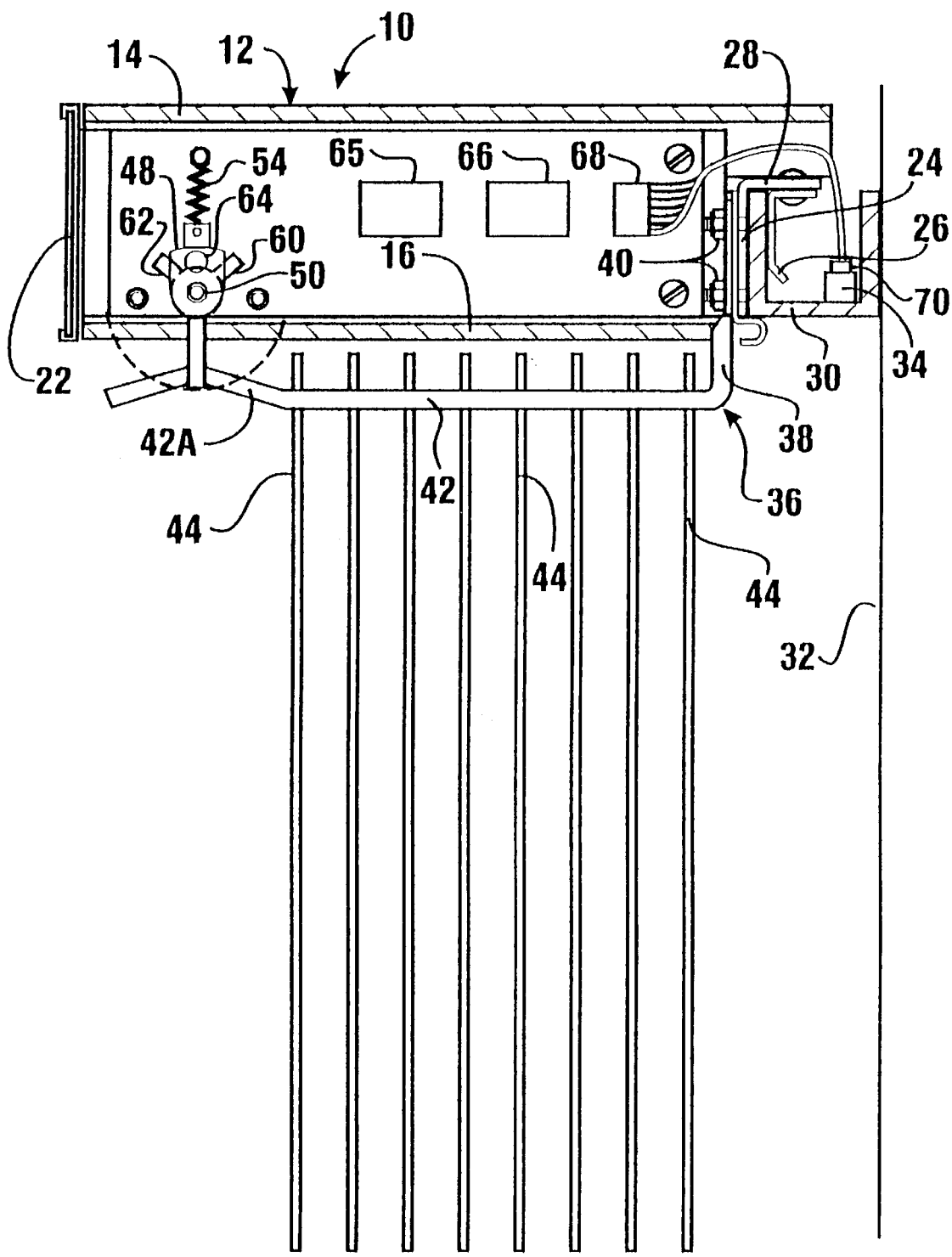
FIG. 1 is a side cross sectional view of an inventory monitoring apparatus called a hook register used in the system of the present invention.
Figure 2:
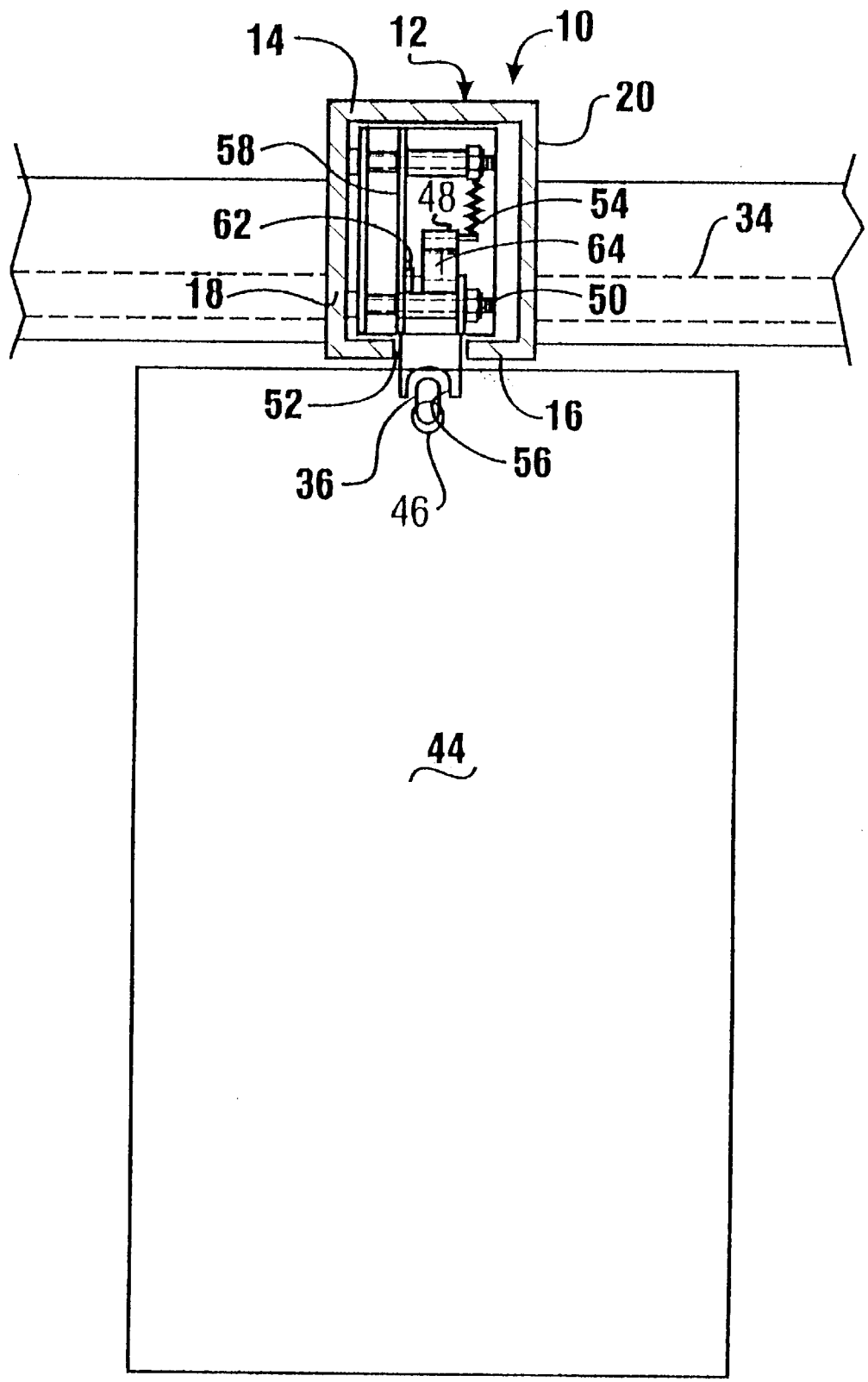
FIG. 2 is a front cross sectional view of the hook register shown in FIG. 1.

Referring now to the drawings and particularly to FIGS. 1 and 2, there is shown therein a first embodiment of an inventory monitoring apparatus of the present invention referred to as a hook register and generally designated by reference numeral 10. Apparatus 10 includes an elongated housing 12 including an upper wall 14, a lower wall 16, side walls 18 and 20, a front wall 22 and a rear wall 24. Housing 12 may be formed of any suitable durable material such as plastic or metal. A clip assembly 26 or similar attachment mechanism is desirably carried by a flange 28 of rear wall 24 whereby the housing may be detachably fastened to a rail or similar support structure 30 affixed to a wall 32 or like surface. As will be discussed in greater detail hereafter, rail 30 may also carry a communications bus 34 or other suitable means for electrically connecting the apparatus 10 to a similar apparatus and to a remote computer and data terminal.

An object support means is designated by reference numeral 36. As illustrated, the object support may assume the form of an elongated rigid or angled rod which may be suitably formed of metal or plastic. A shorter leg 38 of the object support means is affixed such as by threaded fasteners 40 to the rear wall 24 of housing 12. A longer leg 42 of the object support means extends generally longitudinally of the housing 12 and is capable of supporting a plurality of objects 44. Thus, according to the first embodiment, object support means 36 resembles an elongated peg or rod which suspends objects 44 from holes or perforations 46 provided therein (see FIG. 2). The longer leg 42 of support means 36 also desirably is formed with a raised portion 42A to prevent the objects from unintentionally sliding off the object support means.

It will be appreciated that hook register 10 finds beneficial usage with articles or objects which are suitable for suspension and whose inventory it is desirable to monitor. Typical items may include packages containing medical items such as drugs, medical equipment, supplies, including for example, catheters and guide wires for angioplasty or other medical items which should be strictly and accurately monitored because of theft, safety, critical need or other concerns. For this reason, the object support means may assume any form necessary or desirable to support the objects supported thereby. That is, the object support means may be configured as a rack, multiple hooks or pegs or similar cantilevered members, a tee bar or other such equivalent constructions.

A switch actuating means 48 desirably configured as a pivotable lever is mounted generally at its midpoint to housing 12 by a pivot pin 50. In the preferred embodiment, a first end of lever 48 projects through an opening 52 in lower housing wall 16. It is also contemplated that lever 48 may be adapted to project through an opening similar to opening 52 and may be provided in any other wall of housing 12 so long as those components necessary for the proper functioning of the apparatus 10 are correspondingly repositioned to accommodate the desired orientation and operation of lever.

A second end of lever 48 is connected to suitable biasing means 54 which in the preferred embodiment is a spring. In the preferred embodiment, the biasing means is a tension spring, however in other embodiments biasing means such as torsion springs, compression springs, elastomeric means or the like may be used. The biasing means normally biases the lever to a "inoperative" position in which the lever extends generally traverse to the longer leg 42 of the object support means 36 of the hook register as depicted in FIG. 1.

It is important that the first end of lever 48 sufficiently project from housing 12 whereby it may be contacted and displaced by a medical item 44 which may be either added to or removed from the object support means. To assure that the lever will interfere with the passage of an object, either into or out of a location on the object support means, a first end of lever 48 is provided with a notch 56. Notch 56 is configured to receive the longer leg 42 of the object support means 36 therein. As a result, when a medical item is removed from its storage location on the object support means, the object contacts and then displaces the lever so as to rotate it outward. The object then passes the lever and once this occurs the biasing means 54 returns the lever to the inoperative position.

A printed circuit board 58 is mounted in the interior of housing 12. Apart from certain circuitry components specifically identified below which are essential to provide an adequate appreciation of the operation of the hook register, it will be understood that circuit board 58 includes printed circuitry and other circuitry components.

Electrical switch means are supported by and electrically connected to the circuit board 58. During operation the switch means serve as part of a sensor that generates signals indicative of the placement of objects into the storage location on object support means 36 or removal of such objects from the storage location. The preferred embodiment of the hook register utilizes a pair of switch elements 60 and 62 as the electrical switch means. In the preferred embodiment, the switch elements are Hall-effect sensors which change states (off-to-on) when a magnetic field is detected within close proximity. Lever 48 carries a compact permanent magnet 64 which serves as an actuator means. The magnetic field produced by magnet 64 is capable of being sensed by switches 60 and 62 to affect changes in their status. The signals indicating changes in the status of the switches are detected by a signal processing circuit 65 which converts the signals to an appropriate form to be received and counted by a microprocessor 66. The microprocessor 66 in the hook register serves as a counter which stores a count therein as later described.

Figure 3:
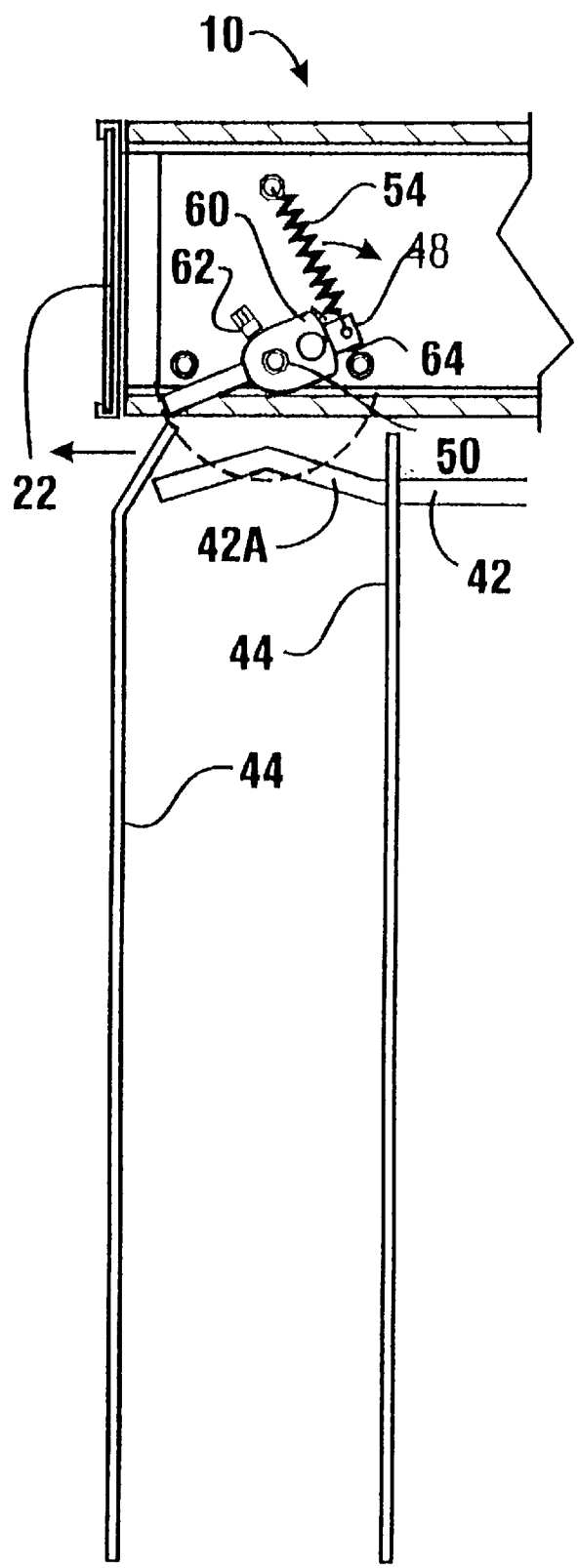
FIG. 3 similar to FIG. 1 depicting a medical item being removed from the hook register.

Operation of the hook register 10 is graphically represented in FIG. 3. Specifically, the object 44, which is preferably a medical item, is shown at the instant in time when it has fully deflected the lever 48 against the force of the biasing means 54 and has just passed the first end of the lever. At this moment, the permanent magnet 64 is pivoted into a substantially facing relationship with magnetic field detector switch 60. Switch 60 is triggered upon detection of the magnetic field in proximity to the switch element and generates a signal indicating that one object unit has been removed from the object support means 36. Once the medical item has passed off the object support means, the biasing means returns the lever to the inoperative position.

Similarly when a medical item is placed on to the object support means 36, the lever 48 is pivoted in an opposite direction. This causes the permanent magnet to trigger the magnetic field detection switch element 62. This generates a signal indicating that one object unit has been added to the storage location on the object support means. Although in the preferred embodiment magnetic field detection switches are used, other suitable switches such as three-way toggle switches, photo sensors, optical encoders, capacitive or inductance sensors and the like may be employed as sensors to achieve and generate the additive and subtractive article registration signals. Likewise, the switch actuating means may assume forms other than a pivotable lever depending on the type of medical item and storage location involved. For example, a linearly reciprocal lever, a flexible flap or non-contact type sensors may be used in other embodiments.

The microprocessor 66 receives through signal processing circuit 65 the signals generated by switches 60 and 62. The microprocessor contains software programs which record and count the state of the switches each time a change is detected. The number and direction of the changes are counted and stored as a count in the microprocessor. In addition, the microprocessor includes a computer program that enables it to be reset upon receipt of signals from a remote location. In the preferred embodiment, the microprocessor also has stored therein a location identifying indicator that is representative of a number and or other data uniquely associated with the particular hook register. Each hook register and other dispensing apparatus in the system of the preferred embodiment has a location identifying indicator associated therewith.

The electronic circuitry of the inventory monitoring apparatus also has the ability to communicate its count information to other components of the system of the present invention. In each hook register, the processor 66 is connected through a ribbon cable 68 which is connected with an electrical coupling 70. Coupling 70 electronically couples with a communication bus 34. In this manner, circuit board 58 is enabled to receive power from a remote power source and is enabled to transmit and receive data through communication bus 34.

Figure 9:
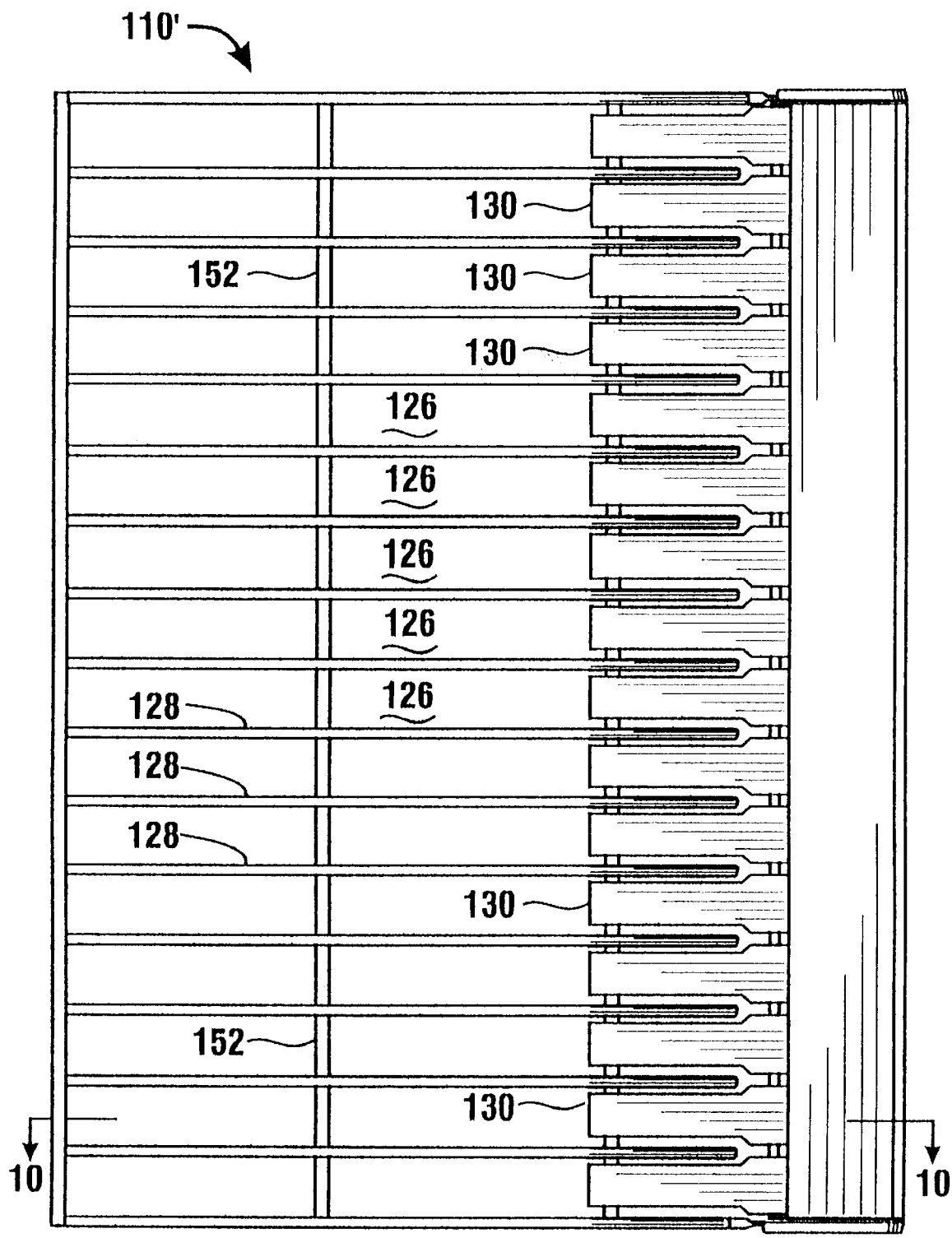
FIG. 9 is a front view of an alternative box register.

The operation of the hook registers 10 in the inventory monitoring and dispensing system of the of the present invention is best shown with respect to FIG. 9. Each of the hook registers is connected to the data bus 34. Each of the hook registers is connected to the data bus 34, which is connected to a hook controller shown schematically as 72. Hook controller 72 includes a processor and a data store therein which are operable to communicate with each of the hook registers 10. The hook controller 72 is operable to periodically poll each of the hook registers 10 on the data bus. The hook controller reads and receives the count information in each of the hook registers and stores it in conjunction with the location identifying information associated with the particular hook register from which the count was received. After the reading of the count information in the register and transmission of the data to the hook controller 72, the count information in the microprocessor 66 may be erased so a new count can be started. Alternatively, the microprocessor 66 in the hook register may be programmed to store the count information and the time each such count was generated for a period of time while generating new count information. This can be done to assure that usage of items from any hook register can be recovered even in the event of the failure of a hook controller. While FIG. 9 shows only four (4) hook registers connected to controller 72, it will be understood by those skilled in the art that many more hook registers may be so connected on the data bus.

As a result of polling each of the hook registers 10, the hook controller 72 has in its associated processor and data store the count of units taken or added in conjunction with the identifying information associated with each hook register. The hook controller 72 is connected by a further data bus 74 to a data terminal 76 sometimes referred to hereafter as a display terminal. Of course other hook controllers and controllers connected to other types of registers may also be connected to data bus 74. The data bus 74 is used to transmit and receive information from the connected controllers to the data terminal 76.

Data terminal 76 includes a display screen 78 which serves as a data output device. In the preferred embodiment, screen 78 is a "touch screen" of the type known in the prior art wherein a user may input data by placing a finger adjacent to icons displayed on the screen. Sensors overlying the screen sense the position of the finger and convert it to input data. As a result, touch screen 78 serves as a graphical user interface which includes a data input device as well as a data output device. Data terminal 76 in the preferred embodiment further includes a card reader 80. Card reader 80 may be used to read data encoded on a magnetic stripe of a user's identification card. Of course in other embodiments of the invention other equivalent reader means for reading coded objects or for reading a user's fingerprints or retina pattern may be used depending on the level of security desired.

In the operation of the preferred embodiment of the invention, a medical technician who wishes to operate the system and remove medical items from the hook registers 10 operates the display terminal. The terminal screen outputs a visual prompt for the user to identify himself or herself to the system by input of identifying data. In certain embodiments, the identification may be accomplished by the user inputting an identification number assigned to the user by touching the appropriate numbers on a graphical keypad presented on the screen of the display terminal. In other embodiments, the user may be requested to swipe their card in the card reader so that the magnetic stripe thereon may identify the user to the terminal. In embodiments where high security is required, a user may be requested to input both their card and a personnel identification number (PIN) into the display terminal. The PIN has a predetermined relationship to the data on the card, and the data terminal may be operated further only if a proper card and PIN are input.

When a user enters their identifying information at the display terminal, the display terminal communicates through a local area network (LAN) 82 to a remote computer 84 which includes a processor and a data store therein schematically indicated 85. Computer 84 has preferably greater and faster processing capabilities and more memory than a display terminal. The computer 84 has stored therein or in another computer operatively connected therewith, information records associated with authorized users. If the data input by the user at the display terminal corresponds to a record for an authorized user, then the display terminal will enable the user to operate the system. In alternative embodiments of the system, one or more display terminals may have the additional processing capabilities and the additional memory to perform the functions of computer 84. In such cases the functions performed by the computer 84 may be distributed among the display terminals, or among a network of numerous display terminals and computers.

Upon further use of the display terminal, the user may access certain information about patients, procedures or physicians which is stored in records in the data store of the computer 84 or other computers connected to computer 84 through a local or wide-area network. In the preferred embodiment, the stored records include information about patients. The user may select a particular patient at the display terminal. This is preferably done by the user scrolling through a displayed list of patient names using "keys" presented graphically on the touch screen. The preferred embodiment of the input device includes appropriate programming of the display terminal to include a highlighting device responsive to a user bringing a finger adjacent to an area of the touch screen indicating the patient or other data selected. The selected item is highlighted to indicate it has been selected and further processing will use the highlighted data. However, other input devices for selecting a patient name and other input data may also be used.

Figure 28:
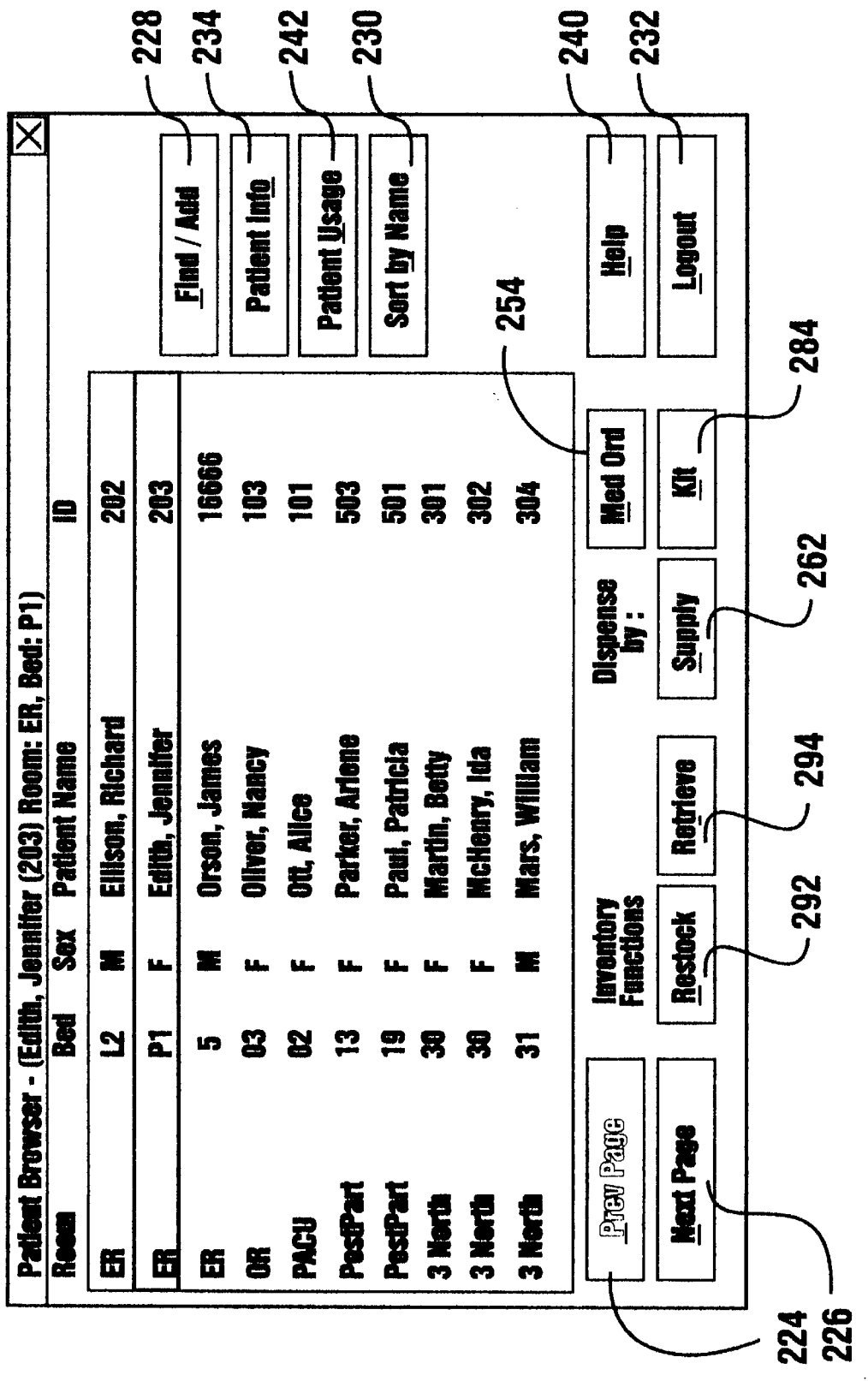

In a preferred embodiment, the display terminal displays a patient browser window 222 shown in FIG. 28. The patient browser window includes a list of patients. These patients are preferably patients that are assigned to patient rooms or other areas assigned to the display terminal through programming in the display terminal or the computer 84. Alternatively, the display terminal or connected computer may be programmed to display a list of all patients in an institution at the display terminal.

The patient browser window includes a previous page button 224 and a next page button 226 that enables a user to review or "scroll" through the stored list of patient names which covers several "screens." Of course, the "buttons" are preferably areas on the touch screen produced by the display to direct the user to touch an area which causes the display terminal and/or connected computer to execute a particular function.

Patient browser window 222 further includes an add/find button 228. The add/find button 228 enables a user to either add a patient to the system or to find a patient already in the system. Upon pushing the add/find button 228 the user is presented with another screen which prompts the user to indicate whether they wish to add a patient or look for a patient who is already in the system, perhaps in another area of the institution. Further screens are presented based on the selection input by the user. For example if the user wishes to find a patient, a screen will request the user to input information about the patient such as the last name. The user may be provided with a representation of a keyboard on the touch screen for this purpose or the display terminal may be connected to an alternative input device such as a keyboard. Upon completion of the input of information, the user indicates that the input is complete through the input device. The connected computers are then operative to attempt to find records related to such a patient and display the information on the touch screen.

Alternatively a user may press a sort button 230 to attempt to find a patient. The display terminal and connected computers are operative to sort the list of patients by name and display the sorted list on the touch screen of the display terminal as shown in FIG. 28. Touching the sort button changes the manner in which patients are displayed on the touch screen. For example, touching the sort button may cause it to change the screen so that patients are displayed sequentially by room. The designation on the sort button 230 correspondingly changes as it is togged to indicate how patients are being displayed.

Alternative displays may also be provided in connection with the sort button 230 by programming the computer and the display terminal to sort and display patient data from various patient records in different ways. These may include for example sorting patients by area or ward, by physician, by gender and in other ways that are useful to users of the system. Each time the sort button 230 is touched or "toggled" a new sorted display of patients or information is provided on the touch screen and the designation on the sort button changes to correspond with the method of sorting. The sort button repeats the sequence after it has been toggled through all the sort options.

Returning to a discussion the functions associated with add/find button 228, after first pressing this button the user is presented with another screen where they may indicate that they wish to add a patient. By providing this indication to the display terminal through an input, the user is prompted by screens presented on the display terminal to input the information needed concerning the new patient. The user can input the information through an input device such as a representation of a keyboard on the touch screen of the display terminal, or through an input device such as a keyboard attached to the display terminal.

The display terminal and connected computers are programmed to prompt the user to input the necessary information to add at least one record for the patient to the database of the system. The inputs may also include optional information about the patient as may be available. After inputting the information the display terminal prompts a user to institute an "enter" command which adds the patient and associated information to the system.

In response to the patient information being entered, the connected computers are operative to establish records for the patient in accordance with their programming. They are also operative to establish programmed correlated relationships among records and/or items of stored data related to the new patient. Further in accordance with programming of the system, the system may prompt users of other types of terminals or other data input stations to generate records or input data into records concerning this new patient.

Upon finding the desired patient name in a patient window such as window 222, the user designates that patient's record by touching the patient's name on the screen. Thereafter, the user may remove medical items from the hook registers that are needed by that patient. When this occurs, the number of units of each item removed from a particular hook register is stored as a count in the microprocessor in each hook register. This information is then transferred to the hook controller 72 when the hook register is polled, and is thereafter transferred to the data terminal 76 when the hook controller 72 is accessed through the data bus 74 by the data terminal. As a result, data representative of both the patient and the location and number of units of medical items used for that patient is available in the data terminal.

When the user signs off the data terminal which is done by pushing a log-out button 232, or selects another patient (indicating that the items for the prior patient have been taken), the data terminal then transmits the information corresponding to the counts and location numbers of the items used for the selected patient through the LAN 82 to the data store in the computer 84 or another operatively connected computer or data store. The computer 84 functions to correlate the count and location numbers with a medical item record which indicates the types of items stored and the location. This provides an indication of what was used for the patient. In addition, the processor and memory in the computer 84 serve to update the record related to the patient to indicate that the items taken were used for the patient so that the patient may be charged therefore. The location records related to medical items preferably includes or may be referenced to pricing information so that patient may be automatically billed. In addition, the computer 84 also updates its records concerning the number of medical items remaining in storage in each location.

The computer 84 is operable in the preferred embodiment to maintain a continuous real time record of how many units of medical items are stored in each of the locations. If the number remaining in any location has reached a lower limit, the computer 84 is programmed to provide a warning of the need to replenish the supplies at that location to an administrator terminal or workstation 86. The administrator's workstation 86 is also a computer with a processor and data store and is connected through the LAN. It has input devices such as the keyboard and mouse shown and an output device such as the screen shown. The terminal 86 may also have other input and output means such as a touch screen, spoken word recognition, audio output or signal outputs connected to printers or other devices. Of course, the need to replenish the supplies may be indicated on the screen at the administrator's workstation or in other output locations including the data terminals in the area where the hook registers need to be replenished.

In other embodiments, the data terminal may be used to help medical technicians or nurses select medical items for patients. The computer 84 or other connected computers have associated data stores which include records which contain information on medications prescribed for patients. The computer 84 also preferably includes records related to medical procedures as well as physicians in its data store. This information may be accessed at the display terminal by the medical technician or nurse who is obtaining supplies for use in such a procedure. By accessing the stored data records related to the procedure, the technician can read a record which includes information such as the items that are normally used in such a procedure. As a result, the technician may note these items and may remove them from the hook registers while viewing the procedure record to ensure that everything normally needed is transferred to the operating room. In addition, the procedure records may be accessed in connection with a physician record related to a physician who will perform the procedure. Such records may include additional medical items that the particular physician requires to have present in an operating room when conducting a particular procedure. This may include additional medical items or particular types of medical items that the physician prefers. It may also include convenience information such as the particular type of music the physician prefers to have played in the operating room during a procedure or other items that the particular physician prefers to have available.

In other embodiments of the invention, computer 84 or other connected computers may be programmed to have in its data store, and may provide in response to a request at a display terminal, a schedule of procedures in a particular hospital operating theater. This enables the medical technician or nurse participating in the procedure to locate the patient scheduled for a procedure using the display terminal, and to access therewith the records related to the physician and the medical items that will be needed for the procedure. As a result, the technician or nurse may go to the hook registers, obtain the necessary medical items and have them immediately charged to the patient's account. Alternatively, if medical items which are dispensed are involved, the items may be simultaneously dispensed together. If after the procedure not all of the items that were originally taken were used, the items may be returned to inventory and credited to the patient's account if appropriate. Alternatively, such items that are partially used may need to be wasted. This is generally done by the user identifying himself or herself to the display terminal 76 and again identifying the patient to the system using the touch screen 78 in the manner previously described. Replacing the unused items back on the hook registers 10 automatically creates a record that such items were returned and the patient's account will be credited in the computer 84. Alternatively returned medications and wasted items are returned to designated areas and records thereof are generated and stored.

Because of the large number of records that are stored in the data store of the computer 84 and other connected computers, a large number of reports related to inventory usage may be generated. This can be accomplished by using database software such as Paradox® in computer 84. Alternatively, other relational database software such as Oracle® may be used. Further, because the inventory at each location is monitored, messages requesting transfers of inventory from areas where there are excess units to areas where there is a need can be automatically generated by the computer and displayed at the administrator's workstation. The computer 84 also keeps a running tally of what has been used by each patient as well as what has been taken by each user and used by patients of each physician. This further allows monitoring of usage and allow potential abuses to be uncovered. The computer 84 is ideally programmed to look for patterns of dispensing activity that have been programmed into the computer's memory as potential abuses and to display a report thereof at the administrator's workstation. Such potential abuses may include taking particular items at abnormally frequent intervals. The computer 84 may also be programmed to provide reports from the database concerning what particular users have dispensed during a given time period and what particular physicians have used or prescribed for patients.

In the preferred embodiment of the system of the present invention, the administrator's workstation 86 is used as the primary tool for the monitoring of inventory. The administrator's workstation is used to program the particular type of medical item stored in the location at each of the hook register and in other types of registers in the system. This is done by creating a record for each location in the data store. The administrator's workstation is also used to set the level of the minimum acceptable number of units of each item at each location so that an indication may be given of a need to replenish or transfer stock. This is programmed as a minimum for each location, and an indication is given when the minimum is reached. Further, the administrator's workstation preferably includes electronic ordering capability so that when supplies of a particular item are reduced to a particular level, a purchase order to replenish the stock is sent automatically to the manufacturer. The ordering and source information is also optimally part of or referenced with the associated record with the item in the data store. As a result, the administrator's workstation is programmed so that when the quantity of an item on hand falls to a particular level, an order is communicated to the manufacturer of the needed item directly over a telephone or other data line via a modem, indicating electronically the item needed, an order quantity and a date by which the items must be received. The order quantity data may be preprogrammed or may be calculated automatically by the computer using a program that generates the order quantity based on rate of use. Likewise, the delivery date may be a programmed time period after issuance of the order, but may also be programmed to be a rush order if the "on hand" quantity has fallen to a second lower level or if the use rate is above a programmed level.

The administrator's workstation may also be used to establish records for authorized users and to set varying levels of security for authorized users at different types of display terminals. Although in the preferred embodiment, the administrator's workstation is the primary control for the system of the present invention as shown in FIG. 9, the hospital's other computer systems including the admission-discharge-transfer (ADT) system 88 and the hospital information system (HIS) 90 are also connected to the local area network 82. This enables the patient data in the computer 84 to be input and output to the ADT system 88 and records relating to patient activity or other activities to be received from or stored in the HIS, which is typically the long term data storage facility related to patients. The system is also preferably connected to other computer systems in the institution such as a pharmacy system 89 which provides information on medications prescribed for such patients. The system may also be connected systems in dietary and food services and in other institution areas. Each of these systems may contain multiple processors and data stores which transmit selected data to and from the LAN 82. This enables the exchange of data throughout the hospital's computers which facilitates both record keeping, patient billing and monitoring of its inventory.

Figure 4:
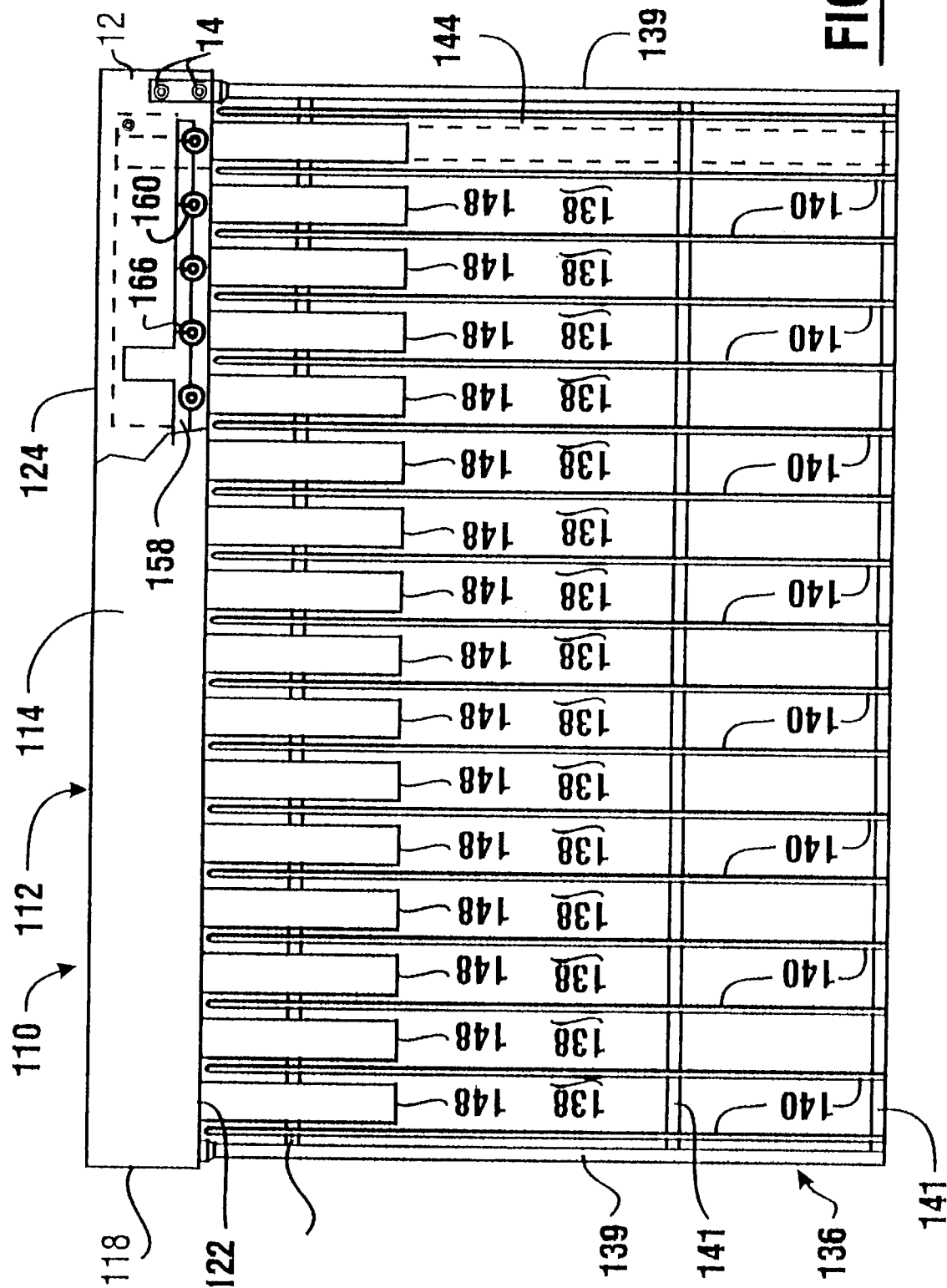
FIG. 4 is a partial cut-away top plan view of a further inventory monitoring apparatus of the present invention called a box register.
Figure 5:
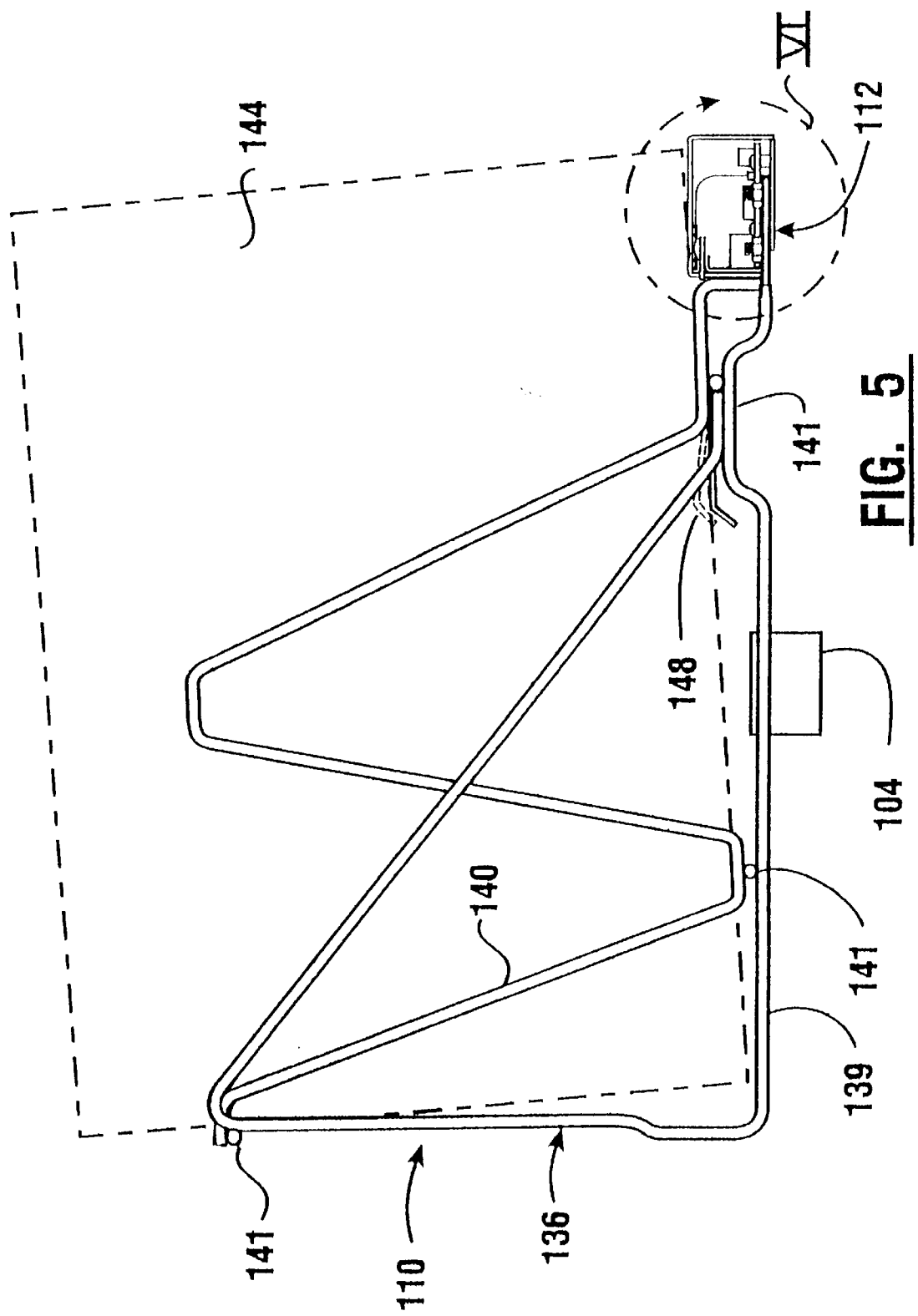
FIG. 5 is a side elevation view of the box register shown in FIG. 4 as seen along line v—v of FIG. 4.
Figure 6:
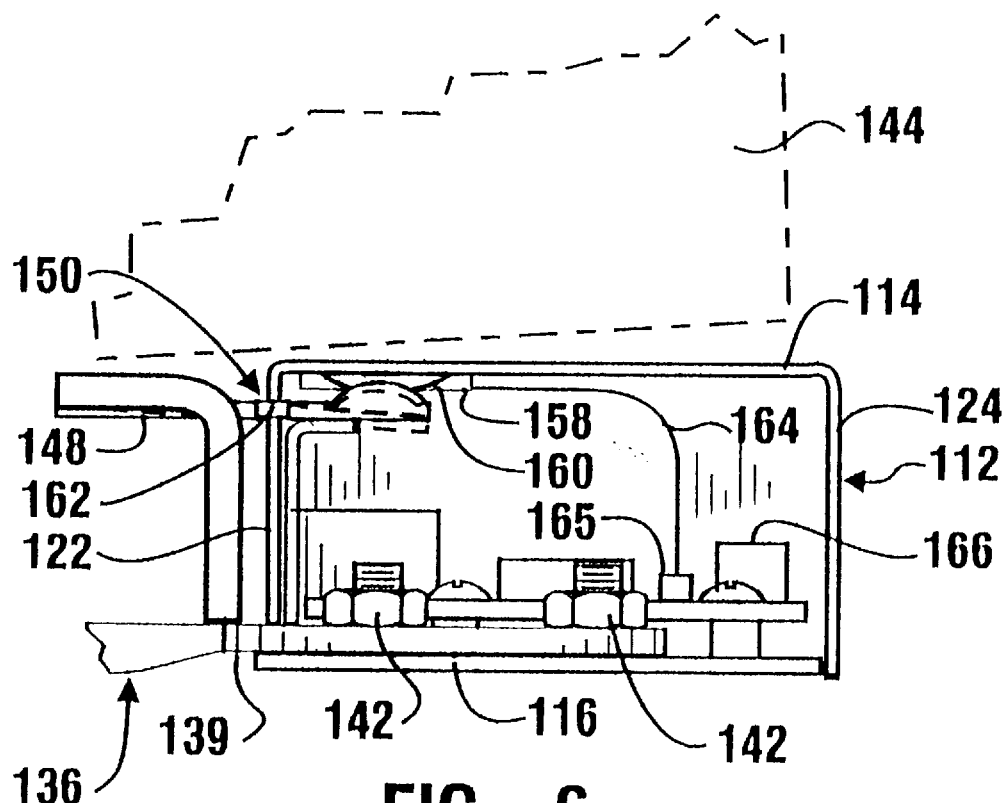
FIG. 6 is an enlarged view of the circled portion VI shown in FIG. 5.

The hook registers 10 which are optimally constructed for supporting hanging items are only one type of dispensing device that can be used with the present invention. FIGS. 4 through 6 reflect a further embodiment of an inventory monitoring apparatus designated by the numeral 110. Apparatus 110 is called a box register as it is optimally adapted to include storage locations for holding boxes or box-like articles. Box register 110 includes an elongated housing 112 including an upper wall 115, a lower wall 116, end walls 118 and 120, a front wall 122 and a rear wall 124. Like housing 12 of hook register 10, housing 122 may be fabricated from any durable material such as plastic or metal. Although not shown, it will be understood that a clip assembly similar to clip assembly 26 of FIGS. 1 and 2 or a similar attachment mechanism may be used to detachably fasten the housing to a wall. Alternatively, apparatus 110 may rest on a level shelf, tabletop or reside in a cabinet. Each box register 110 is connected to a communication bus 74 (see FIG. 9).

With regard to the box register, in this embodiment, an object support means is represented by reference numeral 136 which support means may assume the form of a receptacle having at least one or preferably a plurality of compartments or object storage sites 138 which are locations wherein medical items may be stored. In this embodiment, object support means 136 is constructed as a multiple compartment, heavy gage, stiff metal wire rack including a pair of upright truss-like end walls 139, a plurality of spaced apart storage site divider walls 140 situated between and generally parallel to the end walls 139 and a plurality of transverse members 141 affixed to the end walls 139 and divider walls 140. The end walls 139 are desirably secured by suitable mechanical fastening means 142, such as nuts and bolts or the like to lower wall 116 (as shown) or any other wall of the housing 112.

As shown in the figures, the object support means 136 is adapted to support objects 144 of substantially uniform dimensions (one of which is shown in phantom in FIGS. 4 through 6) in a substantially upright orientation. For example, objects 144 may be generally uniformly sized relatively thin boxes or similar packages which may contain various designated types of medical products. The object support means as illustrated is thus capable of supporting an object on four sides thereof, i.e. the bottom, back and both lateral sides of the object (see FIGS. 4 and 5). In this fashion, an object 144 may be removed from the object support means 136 by lifting it forward (to the right as shown in FIG. 5) and/or upward. The bases of the divider walls 140 are situated at a lower elevation than the upper wall 114 of housing 12 (FIG. 5) whereby the objects 144 are caused to be tilted slightly rearwardly such that the back sides of the objects maintain contact with the rear of the object support means 136.

Although the described embodiment of the object support means 136 supports the objects 144 such as boxes in substantially upright or vertical position, the present invention also contemplates rack geometries whereby objects may be supported substantially horizontally, at acute angles or in a staggered array incorporating one or more angular support orientations. Further, the spacing between the divider walls 140 need not be uniform in which case storage sites 138 of variable dimensions may be provided in the same object support means 136. Of course the object support means 136, like housing 112, may be fabricated of metal or from any high strength substantially rigid plastic or other suitable material.

Box register 110 includes switch activating means 148. The switch activating means 148 includes one or more levers pivotally mounted at 150 (see FIG. 6) to housing 112 in a manner described hereafter. The levers 148 correspond in number to the number of compartments 138 which are the storage locations provided in the object support means 136. A first end of each lever 148 projects from the housing 112 into a respective one of the storage sites 138 and a second end of each lever extends into the housing as most clearly seen in FIG. 6. The first end of each lever protrudes from the housing for a distance sufficient to be contacted and displaced by an object 144 when such object is added to the object support means 136. Biasing means later discussed return the levers to inoperative positions upon removal of an object from the corresponding storage site.

Referring to FIGS. 4 and 6, as is the case with the hook registers described above, the box registers likewise have printed circuit boards therein designated 158 one of which is shown. Circuit boards 158 are mounted in the interior of housing 112. Circuit boards 158 include printed circuitry and other circuitry components which are not illustrated or described in detail except to the extent necessary for a proper understanding of the present invention.

Electrical sensor means are supported by and electrically connected to circuit board 158. The sensor means generate signals indicative of the placement of an object onto and the removal of an object from the object support member 136. According to the preferred embodiment, the sensor means comprises one or more discrete force actuatable switches 160 such as snap-type internally resilient dome switches or other type electrical switches. Switches 160 are spaced apart along the length of circuit board 158 and correspond in number to the levers 148 whereby the second end of each lever operates a separate switch.

The switches 160 generate real time counting signals indicative of the total inventory of objects 144 carried by the object support sites which are occupied and those which are unoccupied at any instant in time. Thus when a lever 148 is caused to pivot in one direction by an object that is placed into a storage location, the second end of the lever closes its respective switch 160. This is reflected by the solid line image of lever 148 depicted in FIGS. 5 and 6. Switch 160 in turn generates a registration signal indicating that an object has been placed into the storage location and at which storage site the object has been added.

Conversely, when an object is removed from the object support means, the biasing force from the internal resilience of the dome switch 160 returns the lever to its inoperative position as is reflected by the dash line image of lever 148 illustrated in FIG. 5 and 6 whereby the switch is open. In this position, the switch generates a registration signal which reflects that an object has been removed from the storage location. Additionally, if mechanical switches other than dome type or other similar switches possessing internal resiliency are employed as the electrical switch means, then biasing means such as springs or elastomeric means may be provided to assure that the switches change electrical condition upon removal of objects from the object support means 136. Alternatively, certain switch types have built-in springs which provide the biasing force. Although dome type switches are used in embodiments of the box registers, other suitable sensor means such as two-way toggle switches, momentary contact switches, photo sensitive switches, capacitive or inductance sensors and the like may be employed to affect the generation of additive, subtractive and object locating registration symbols.

Figure 7:
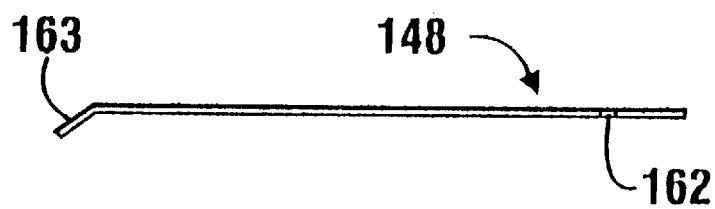
FIG. 7 is a side view of a lever used in the box register shown in FIGS. 4 and 5.
Figure 8:
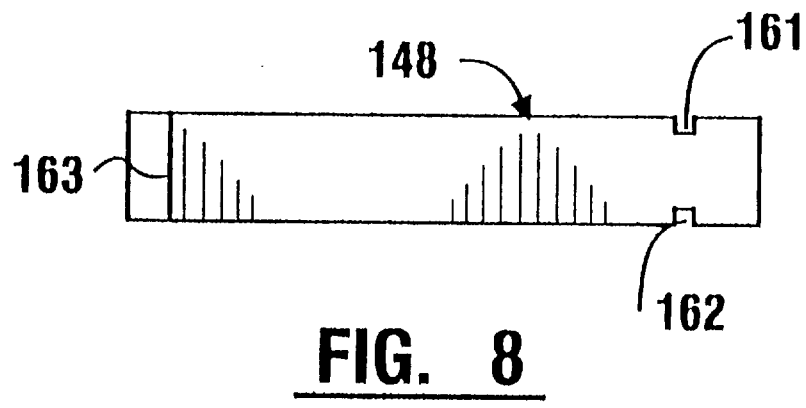
FIG. 8 is a top plan view of the lever shown in FIG. 7.

FIGS. 7 to 8 show on an enlarged scale a lever 148. The lever desirably includes a pair of opposed notches 161, 162 which generally separate the lever into its first and second ends and, in cooperation with mating slots provided in the front wall 122 of housing 112, establish the pivotal connection 150 of the lever relative to the housing. Further, each lever 148 is preferably provided with a downwardly sloping lip 163 at the leading edge of its first end to facilitate insertion of the objects 144 into the storage sites 138.

The signals indicating changes in the status of the switches 160 are transmitted by wire or other acceptable signal conducting means 164 whereupon they are detected by a signal processing circuit 165 which converts the signals to an appropriate form to be received and counted by a microprocessor 166. The microprocessor 166, like microprocessor 66 of the hook registers 10 described above, contains software programs which record the state of the switches each time a change is detected. The microprocessor 166 also counts and stores a count indicative of the number and direction of changes in state as they occur. Further, the microprocessor 166 includes the unique location identifying indicator associated with each of the storage locations in which any changes in the presence of a medical item have occurred. Alternatively, the microprocessor 166 may keep track of the times such changes have occurred.

While not illustrated it will be appreciated that the hook and box registers are preferably remotely powered through the associated bus connections. In other embodiments they may be locally powered. Further, in other embodiments the registers may include LED or LCD displays on the registers for indicating the powered condition of the particular register or the fact of a change in the status of inventory items at the location. Of course suitable LED or LCD indicators may also be used for other purposes such as indicating the particular type of item to be stored, that the register is in a restocking mode, or that the amount of inventory stored in the location has fallen below a critical level. This is accomplished by programming in computer 84, or programming in the other processors connected to LAN 82 to output such an indication under such conditions.

An alternative embodiment of a box register 110' is shown in FIGS. 9 through 12. Box register 110' is similar to the previously described box register 110 except as expressly noted herein. The box register 110' includes a plurality of compartments 126 which are separated by divider walls 128. Each compartment has located therein a lever 130, which is movable about a pivot 132 (see FIGS. 11 and 12). The lever includes an object engaging leg 123 and a switch actuating leg 133. The leg 133 is engageable with an actuating projection 134 of a switch 135. The switch 135 includes an internal spring which biases the actuating projection outward from the switch. The switch operates to change its electrical condition when the actuating projection is depressed.

Objects or items such as boxes holding medical supplies are stored in the compartments 126. The presence of an object in the compartment engages the object engaging leg 123 and moves the associated lever 130 to the position shown in phantom in FIG. 11. In this position lever 130 is in abutting relation with a stop member 152 which bounds the rear of the compartment. The stop 152 prevents the object engaging leg of lever 130 from being rotated rearward beyond the position shown in phantom. When object engaging leg 123 is in engagement with stop 152, switch actuating leg 133 depresses actuating projection 134 of switch 135 resulting in the switch having a first electrical condition.

Upon removal of the box or other object from the compartment, actuating projection 134 moves outward in response to the biasing force of the internal spring as the object disengages lever 130. Outward movement of actuating projection 134 causes switch 135 to change its electrical condition. As in the earlier described embodiment of the box register this change is noted in conjunction with the location information in the box register's associated microprocessor, similar to microprocessor 166.

Although the box registers shown are a single tiered rack, the object support means may comprise a multi-tiered rack or a plurality of rows and/or columns of cubicals whereby each of the storage sites or cubicals may be appropriately fitted with a switch actuating means such as a lever.

In the preferred form of the invention, the box registers are connected through bus 74 with the display terminal 76. The display terminal periodically reads the count information in the microprocessor 166 associated with each of the box registers and receives changes in the count information associated with each of the storage locations in the box registers.

A user may operate display terminal 76 to indicate the appropriate patient for which material taken from the box registers will be used in the manner previously described with regard to the hook registers. In addition, the administrator's workstation is used in the setup of the system to assign the particular type of medical item to be stored in each location in the box registers which is stored in a record in computer 84. However, unlike the hook registers which may store a substantial number of units of the particular type of medical item in each location, a box register is adapted to store only one such item in each location. Therefore, in some embodiments several adjacent locations in the box register are designated for containing the same type of medical item.

As is also the case with the hook registers, a user of the system who is replenishing inventory to the box registers may operate the display terminal to so indicate using the touch screen data entry device that he or she is replenishing inventory. In this case, the records in computer 84 will be updated to indicate the units of inventory added in each of the storage locations. No patient is credited for the items stocked in the locations and a record in the data store concerning the number of such items on hand but not yet placed for use in a location is also updated. In alternative embodiments, a bar code is applied on the various items stored in the hook and box registers. A bar code reader or scanner shown schematically as 104 in FIG. 5 is positioned in the hook and box registers so that the code on the item is read as it is placed or removed from a location. The bar code scanner generates signals that are interpreted by software for reading bar codes which runs in computer 84 or another terminal in the LAN 82. A data store associated with the software includes information which correlates each bar code identifier with a particular medical item. This provides a check that the item actually stored or taken is the type that is recorded as stored in that location. If an error is made an alarm may be given, either at the register, display terminal and/or the administrator's workstation. Alternatively, the bar code on the medical items may be used to "set up" the system, so that the system records the fact that a particular medical item is stored in a particular location as a result of having read the bar code thereon as the item is placed therein. This avoids the need to program the Administrator's workstation with this information. The bar code scanner can be provided in addition to the indicator which indicates an item is added or removed. Alternatively, the bar code may be read as each item is removed from a location on a hook or box register and the use for the patient of the item recorded directly in response to reading the bar code signals and identifying the patient at the display terminal.

The information included in the data store with respect to particular items may also include a date by which perishable items must be used. The user stocking such items in the locations can input such information using the input device of the data terminal. Items having a limited shelf life are preferably stored in the box registers where the "use by" date can be uniquely associated as part of the record for the only item in the location.

The system can also be used with other types of devices that are used to indicate that an item has been taken for a patient. One such device is a manual input register where a nurse or other medical technician manually indicates that an item has been taken.

In one embodiment a manual register is structurally similar to box register 110' except that it does not include compartments or levers. The actuating projections of the switches are connected to manually engageable buttons. The system is programmed so that the momentary change in electrical condition of a switch resulting from depression of a particular button represents the taking of one unit of a particular item from storage. Preferably each button is labelled with indicia representative of the item that it is associated with.

In the case of a manual register, the nurse or medical technician ques up the patient who will receive the items on the screen of the data terminal and touches the screen to select that patient. The user pushes each button on the manual register corresponding to the type of item taken. By pressing the button once for each unit of an item taken, data is stored in the micropressor associated with the manual register which is representative of the particular button location pushed and the corresponding count associated with that button. This information is correlated with the patient record in the same manner as occurs with the hook registers and box registers.

The system of the present invention may also be used in conjunction with other types of dispensing devices. An example of such a device is an electronic lock drawer 96. The electronic lock drawer may be used to store narcotics or other articles, the use of which is highly restricted and which are not suitable for storage in a hook or box type register of the type previously described. Alternatively, the electronic lock drawer may comprise a secure enclosure housing hook registers or box registers in its interior. The function of the electronic lock drawer is to hold the restricted items and provide access thereto by opening a locking mechanism of the unit only when a set of predetermined conditions are satisfied.

In the preferred form of the invention the electronic lock drawer is connected to and the opening thereof controlled through an adjacent data terminal 98. Data terminal 98 is similar to data terminal 76. Data terminal 98 is connected to the electronic lock drawer 96 and is operable to unlock the lock thereto upon receipt of appropriate signals from computer 84. Of course although only one electronic lock drawer is shown in connection with data terminal 98, additional electronic lock drawers may be connected thereto.

In the preferred form of the invention, information about each type of restricted material housed in each electronic lock drawer is stored in a record in the computer 84. To gain access to these materials a user must first identify himself or herself to the data terminal in the manner previously described. Preferably for highly restricted items, computer 84 requires not only a user to input an identification card and PIN number but also a second authorized user to input their coded card and PIN number. The purpose for requiring two (2) authorized users to be present to open the electronic lock drawer is so that the items removed and their disposition may be verified.

Preferably, the computer 84 has stored in the patient record, information about the medications that the patient has been authorized to be given. As a result, the user may use the data terminal to select the patient name and to request the opening of the electronic lock drawer so the user may take the medication for the patient. This is done using the touch screen of the data terminal as an input/output device. Thereafter, upon proper input of a further authorized user's verification information, the electronic lock drawer will unlock in response to signals sent from the computer 84 to the data terminal 98 and from the data terminal 98 to the lock drawer 96. Thereafter, the user may remove the medication from the lock drawer in the presence of the verification user and reclose the unit. Upon the user inputting a verification input to the data terminal that the medication has been taken, the associated record of use and the charge therefore is automatically added to the patient's account by the computer 84.

It does not matter if a medication that is stored in the electronic lock drawer is not listed as one the patient is authorized to receive in the patient's records in the computer 84, the user may still access the electronic lock drawer. A user may input a request through the data terminal for a listing of medications available. In response the computer 84 outputs to the data terminal a listing of the available medications and the dosages. The computer may also provide information on the location of each medication. The user may then select a particular type of medication and then input through the data terminal a request for a listing of patients which again is provided from the records in the data store of computer 84. By selecting the patient who is to receive the medication (and when appropriate providing the necessary verification from a co-authorized user) the appropriate electronic lock drawer will unlock and allow access to the medication. Upon verification input to the data terminal from the user that the medication has been removed, the computer will charge the patient's account therefore by updating the patient's record. Of course as is the case with the other medical item storage locations previously described, computer 84 also operates to keep track of the inventory of various items inside the electronic lock drawer 96 to assure adequate stock. The computer is also programmed to record the users and verification users who have removed items from the electronic lock drawer and the types of items taken so that any shortages or patterns of abuse may be automatically noted. Further, as discussed previously, data terminal 98 may be used to access information in the computer concerning procedures and physicians so that items in the electronic lock drawer 96 may be taken to an operating theater in advance of a surgical procedure.

Of course data terminal 98 may be used like data terminal 76 to credit a patient's account for items returned from inventory as well as to indicate replenishment of inventory in the electronic lock drawer. If a narcotic substance is to be returned the computer is programmed to have a verification user verify the returns. Returns are preferably made into special one way receptacles so that returned items can not be removed by unauthorized persons.

Another type of dispenser apparatus that may be used in the system of the present invention is the medicine dispenser 100 shown in FIG. 9. Medicine dispenser 100 is also used for dispensing medical items that require high security such as narcotics. However, unlike electronic lock drawer 96, medicine dispenser is operable to dispense only the particular item requested and to restrict access to all the other items housed within the medicine dispenser.

As shown in FIG. 9 the medicine dispenser is connected to a data terminal 102 that is similar to data terminals 76 and 98. The operation of the data terminal 102 in conjunction with the medicine dispenser 100 is similar to the operation of data terminal 98 in cooperation with electronic lock drawer 96. The difference in the use of the medicine dispenser is that in response to selection of the particular medical item (and the co-user verification if required) the medicine dispenser will provide to the user the particular medical item requested in the quantity requested. As a result, the user is not required to locate the item as is required with the electronic lock drawer. In addition, the level of security required for dispense of medical items within the medicine dispenser can be varied depending on the level of security required for the particular item. As a result, for some items in the medicine dispenser 100 it may be necessary only to verify that the user is an authorized user. For other substances, only selected authorized users (and co-users) will be given the substance.

The user interface of the display terminals of the preferred embodiment of the present invention are shown in FIGS. 28 through 37. As previously discussed, after a user accesses the system through the display terminal for purposes of obtaining medical items for a patient, they are generally presented with the patient browser window shown in FIG. 28. From the patient browser window 222 a user may manipulate the previous page and next-page buttons 224 and 226 respectively to display the patient for whom the medical items are to be taken on the screen. The programming of the display terminal includes a highlighting feature which serves as part of an input device of the display terminal. A patient is selected by a user's finger being brought adjacent to the touch screen so as to highlight the patient name as graphically indicated by the highlighted band with a patient name in FIG. 28. Upon touching the patient name in addition to being highlighted, the patient name is also shown at the top of the screen. This serves to identify this particular patient to the system as the one for which medical items are being taken.

From the patient browser screen 222 a user is enabled to remove items from the hook or box registers, in which case the items will be automatically charged to the patient. Similarly if an item taken for a patient is to be returned to a hook or box register, highlighting the patient name on the patient browser screen and replacing the item on the hook or box register results in the patient's records and account being credited for the returned item.

From the patient browser screen 222, more information concerning the selected patient may be obtained by the user touching a patient info button 234. Touching the patient info button 234 causes the display terminal to display the patient information window 236 shown in FIG. 29. Patient information window 236 shows information about the patient. This can include vital statistics, the name of the treating physician, allergies that the patient may have and other information. In addition, the patient information window 236 also shows the assigned location of the patient in the facility. The patient information window 236 includes a close button 238 which a user presses to return to the patient browser window 222.

It should be noted that the patient browser window 222 as well as the patient information window 236 include a help button 240. The help button 240 is pressed by a user when they wish to obtain more information about using the system features that are currently accessed on the displayed window. The display terminal and the connected computer systems are programmed appropriately to provide instructions concerning the type of help most commonly needed when accessing the particular patient windows. This makes the system easier to use and reduces the amount of training required before user may effectively operate the system.

From the patient browser window a user may choose to review the medical items that have been taken for the selected patient. To do this a user touches a patient usage button 242. In response to selection of the patient usage button, the computer and display terminal are operative to display a patient usage browser window 244 shown in FIG. 30. The patient usage browser window is operative to show medications and other medical items that have been taken for the patient as well as the amount and time that each medical item was taken. The patient usage browser window also includes a return button 246 and a waste button 248. The return button is selected in situations where a medication that has previously been taken for a patient is returned without being administered. The return button is used in situations where the returned item is a controlled substance such as a narcotic or is another item that cannot be freely dispensed or used for another patient. Selecting the return button generally enables a particular return drawer mechanism to open into which the medical item may be returned. By highlighting a particular dose of medication on the patient usage browser screen and completing a return transaction, the status of a medication may be changed from taken to return.

The waste button is used in situations where an item taken for a patient is to be returned in whole or in part and it cannot be used for another patient. This includes situations where only a portion of the medication is delivered and the balance is waste. Selecting the waste button 248 also preferably opens a return drawer into which the wasted item may be deposited. The patient's records are simultaneously adjusted accordingly in the patient records and on the patient usage browser window.

The operation of the return and waste buttons 246 and 248, respectively, along with a return drawer used in the preferred embodiment is shown in copending U.S. application Ser. No. 08/679,203 filed Jul. 12, 1996, the disclosure of which Application is incorporated herein by reference.

The patient usage browser window 244 also includes a discrepancy button 250. The discrepancy button is used in connection with dispensing medications as well as with the return and wasting of medications. The discrepancy button 250 is used by a user to indicate to the system that something requested was not provided, or that an indication previously input to the system is not accurate. Pressing the discrepancy button causes the display terminal to display a window appropriate to indicate the nature of the discrepancy. The patient usage browser window 244 also includes a previous page button 224 and a next-page button 226 similar to those previously described for scrolling through the information pertaining to the patient. Window 244 also includes a help button 240 and a close button 238 like those previously described. The close button is used when the user is finished with the patient usage browser window and wishes to return to the patient browser window 222.

Patient usage browser window 244 further includes a trade name/brand name button 252. Button 252 is operative to change the names of the medical items displayed on window 244 from the trade name to the brand name and vice versa. Button 252 may be toggled from one name for an item to the other. This feature is available in a number of windows and is useful for a user who may need to compare the brand name(s) of a medical item to the generic name and vice versa.

Trade name/brand name button 252 is enabled to provide this feature at the display terminals responsive to records stored in data store 85 in which the generic names and brand names for medical items in the system are stored in correlated relationship. The data store 85 further includes in its records data indicative of whether each particular name for the medical item is the generic or brand name. Multiple brand names corresponding to generic names may be stored and displayed on the screen. This feature enables a user operating the display terminal to toggle the display back and forth between brand name and generic name. In addition, the display terminal indicates in a header above the drug information whether the generic or brand name information is being provided on the screen. Button 252 changes to the opposite designation to that being displayed when it is toggled. This informs a user that they can change from, for example, the generic name shown in window 244 to the trade name or brand name by touching button 252 on the touch screen.

From the patient browser window 244, a user is enabled to review medications available for dispense to a patient. To review the medications that have been prescribed for a particular patient, a user highlights the desired patient name by touching the name in the patient browser window 222 and touches a med order button 254. Touching med order button 254 causes a med order browser window 256 shown in FIG. 31 to be displayed. Med order browser window 256 includes information about the medical items that have been prescribed for the patient including information such as dosage and frequency of administration. The med order browser window also contains other information such as the route by which the medication is to be delivered to the patient such as orally or through intramuscular injection. The med order browser window 256 also includes the date and time information that the medication was started. If a medication has been stopped, this may also be indicated.

If a user wishes to take a medication for a patient, the user may highlight the medication on the med order browser window and touch a dispense button 258. By touching the dispense button on the touch screen, the display terminal is operative to cause the electronic lock drawer, medication dispenser or other apparatus in which the particular medication is held to operate to make the medication available to the user. The med order browser window 256 further includes an info button 260. Info button 260 may be pressed to display additional information about the particular medication which has been highlighted. This may include particular information that the physician wished to include concerning the administration of the medication. Alternatively the information button may access information stored in the data store 85 concerning the particular medication itself including information such as possible side effects, drug interaction data and the like.

The med order browser window 256 further includes a trade name/brand name button 252 which may be used to change the displayed drug identification information from generic to brand name and vice versa. Window 256 also includes a help button 240, a previous-page button 224 and a next-page button 226, all of which function in the manner previously described. The med order browser window 256 further includes a close button 238 which a user may select to return to the patient browser window 222.

Instead of reviewing medications that have been specifically prescribed for a patient, a user from the patient browser window 222 may choose to dispense medications and medical items from a listing of all medical items which are available in the area adjacent the display terminal. To accomplish this a user selects a supply button 262 on the patient browser window. Selecting the supply button 262 causes a supply browser window 264 to open on the screen of the display terminal. The supply browser window is shown in FIG. 32. Supply browser window 264 includes a listing of medical items which are available for dispense. A user may select one of these substances by touching the screen adjacent to the item desired. If it is a controlled substance such as a narcotic, the display terminal and associated computers are programmed to require heightened security such as two authorized users to log on to the display terminal before a dispense may be made as was previously discussed.

A user dispenses medical items from the supply browser window 264 by highlighting the item desired and selecting the appropriate select quantity button 268. The select quantity button indicates how many of one particular medical item the user desires to have dispensed. The user then selects the dispense button 258, which is operative to cause the display terminal to actuate the appropriate device for dispensing the requested quantity of item.

The supply browser window 264 also includes the trade name/brand name toggle button 252 previously discussed. The operation of button 252 is demonstrated with regard to an alternative supply browser screen 270 which is shown in FIGS. 35 and 36. Alternative supply browser screen shows only one medical item so as to make more apparent the operation of button 252. In FIG. 35 button 252 is set to display the generic name of the medical item, in which case the single medication shown is displayed by its generic name and button 252 indicates that it is available to be toggled to the trade name. Toggling button 252 changes browser screen 270 to the format shown in FIG. 36 in which the trade or brand name of the medication is displayed, and button 252 indicates that it is available to be toggled to display the generic name. Of course, for medical items for which there is only a generic name, the data base records stored in the data store 85 in connection with computer 84 or other connected computer in the system may be arranged to indicate that there is no corresponding brand or generic name when this situation arises. Likewise for items which have multiple brand names, the display terminal is preferably operative to provide all the brand names associated with the item.

The data store of the system also includes pricing information for both brand and generic medical items. The data terminal and connected computers are operative to charge the patient's account for the type of item which is dispensed. This is determined responsive to the name for the item displayed on the display terminal when the dispense is made.

In some situations the name type for an item prescribed for a patient may not be available in the dispensers connected to the display terminal or otherwise available in the area adjacent the display terminal. The display terminal or connected computer may be programmed responsive to a request to dispense an item by a trade or generic name which is not available, to indicate on the display terminal that the item is available under an alternative name. The user in response to receiving such an indication, may toggle button 252 and dispense the item under its alternative name. In such situations, the user may also consider this a discrepancy which should be recorded in response to the user prompts generated in response to selecting the discrepancy button 250. The ability of the system to track items by both trade or brand names and generic names may avoid needless delay in providing medical items.

Figure 37:
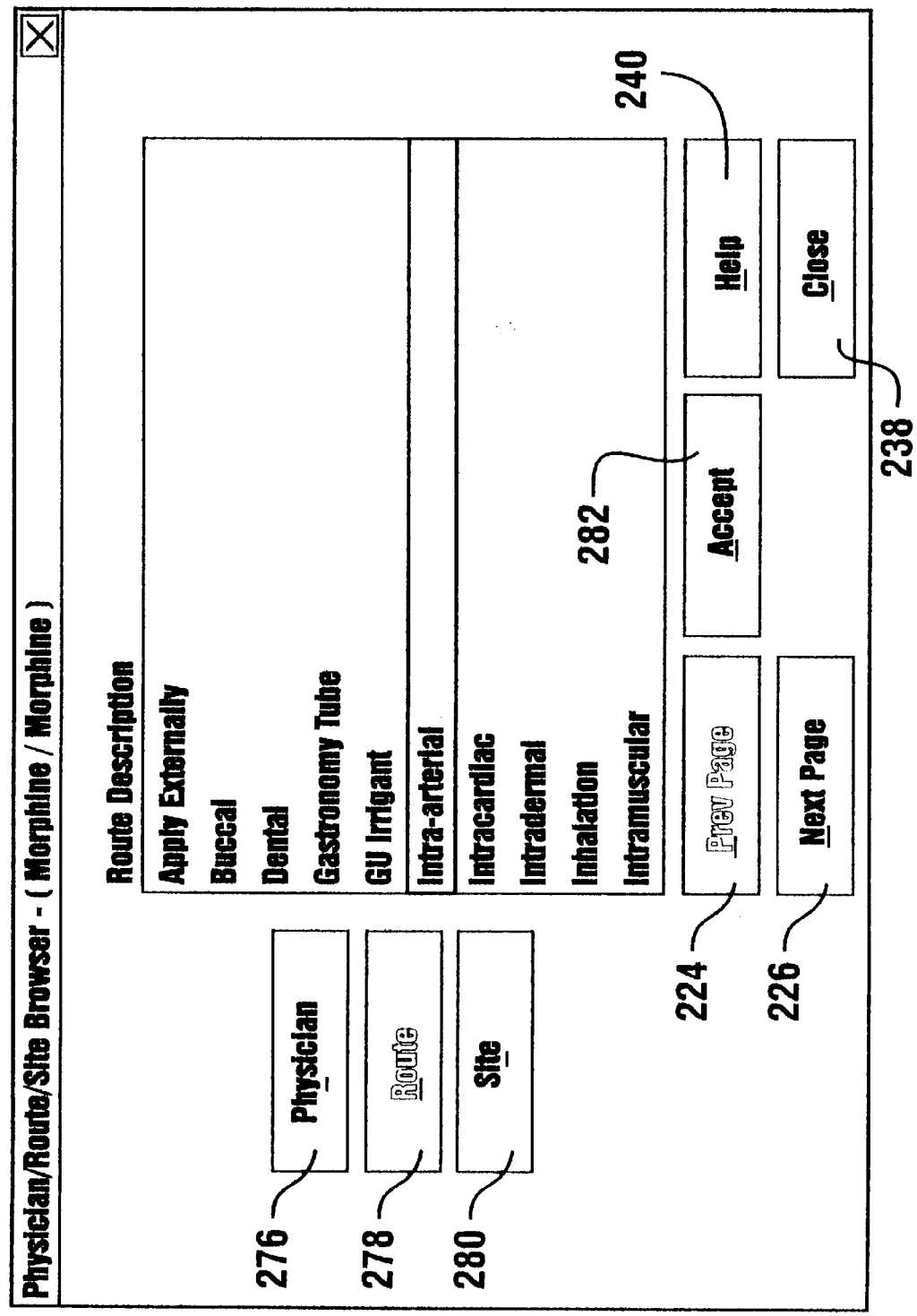

The supply browser window 264 also includes a physician/route/site button 272. Selecting button 272 causes a physician/route/site browser window 274 to be displayed. A sample physician/route/site browser window is shown in FIG. 37. If there is already a physician associated with the dispense of the medication selected in window 264 to the particular patient shown in that window, then a physician button 276 will be highlighted in window 274. If the physician button 276 is highlighted, then a user may press a route button 278 which will cause the display terminal to display a further window which indicates the route that the physician has prescribed for the medication to be administered to the patient. A site button 280 may be selected to review the site on the patient that the physician has prescribed for the medication to be administered. If, however, when the user accesses window 274, the physician, route or site buttons are not highlighted, no associations related to these parameters have been made.

To associate a dispensing order with a physician, a user may select the physician button 276 to display a list of physicians on the screen. The user may then select a physician which causes physician's name to be highlighted. The user may thereafter select the route button 278 which causes a listing of route information, as shown in FIG. 37, to be displayed. The user may then select a particular route by highlighting it. Thereafter, if appropriate, the user may select site button 280, which causes a list of sites to appear. The user may select a site. To save all the associated information that has been input, the user highlights an accept button 282. After reviewing the information in window 274 or establishing a new relationship, a user may close window 274 by selecting close button 238 and returning to patient browser window 222.

As previously discussed, a further advantage of a preferred embodiment of the present invention is that medical items to be used for a particular medical procedure are stored in correlated relation along with a designation of the particular medical procedure in the data store. These collections of medical items are called "kits" in the preferred embodiment of the invention. Kits may be established by the operator of the system in accordance with the particular needs of the system. Kits may include particular collections of medical items for a particular procedure that is scheduled for a patient. Alternatively and in addition, kits may also be a collection of medical items used to conduct particular types of frequently-administered medical tests, such as diagnostic tests.

In accordance with a preferred embodiment to the invention, from the patient browser window 222 a user may review kit information by selecting a kit button 284. Selecting the kit button causes a kit browser window 286 shown in FIG. 33 to be displayed on the display terminal. The kit browser window shows kits that have been prescribed for the selected patient. In addition, the kit browser window preferably displays a listing of other available kits. A user may select a particular kit by touching the kit on the touch screen. If the user wishes to learn what items are in the highlighted kit, they may select a kit info button 287. Selecting the kit info button causes the display terminal to display a kit information window 290 shown in FIG. 34. Kit information window 290 shows the name of the kit and all of the items that are included in the kit. In addition the kit information window shows how many of the particular items in the kit are available for dispense from the storage locations adjacent or attached to the display terminal. The computer may alternatively be programmed either in the kit information window 290 or when a kit is dispensed, to indicate to a user where items that are not available in the area adjacent the display terminal may be obtained. The inventory tracking features of the invention enable providing the user with the nearest location the needed item is stocked.

After reviewing the information concerning what is in the kit, the user may select a close button 238 on kit information window 290 to return to the kit supply browser window 286. The user may select the dispense button 258 in window 286. Selecting the dispense button is operative to cause the display terminal to dispense or make available all the items in the kit together. In addition, the display terminal and connected computers may be programmed to indicate in response to selection of the dispense button that the user is required to manually take from open storage certain medical items that may be required for the kit which are not dispensed. This is accomplished through appropriate programming of the records in the data store when the kit is established. Of course, selecting the dispense button 258 not only causes all of the items in the kit to be dispensed or otherwise made available, but such items are also charged to the patient's account.

The storage of information in the data store concerning kits, which is data representative of collections of items stored in correlated relation for a particular procedure or activity, is highly useful. It provides for automatically dispensing the needed items together where possible, and provides a visual reminder to the user of the system of all the things that are needed to accomplish a particular medical procedure. This avoids mistakes and saves time. Of course, after reviewing the kit browser window 246 and/or dispensing a kit, a user may return to the patient browser window 222 by selecting the close button 238.

After a user has completed dispensing transactions for a particular patient, they may take medications for another patient by highlighting that patient on the patient browser window 222 and repeating the steps for that patient in accordance with the procedures previously discussed. The system is programmed so that a user is free to obtain items either from dispensers of various types in response to dispensing requests, to manually remove items from hook or box register locations or to take items from accessible storage locations. For those items which are controlled substances such as narcotics, dispensing transactions cannot be completed until a second appropriate user or witness enters their identifying information to the system to witness the dispensing transaction. As previously discussed, dispensing transactions which are conducted by a user or a witness are recorded by storing the information on what was dispensed in correlated relation with the user's record as well as with the patient's record in the data store. Of course, the system may be programmed to correlate and store other types of information as well.

When a user is finished with dispensing medications for patients, they may select the log-out button 232 at which point the display terminal waits to be accessed by another authorized user.

It should be noted that the patient browser window 222 also includes a restock button 292 and a retrieve button 294. The restock button 292 is used in connection with restocking the system. Certain system users have correlated records in the data store that enable them to restock the system. Such a user, when they access the data terminal may also select the restock button 292 and cause the display terminal to display windows upon which a user may indicate which items have been restocked, and the available quantities. The person restocking preferably does this by accessing the dispensers and electronic lock drawers using keys or access methods which are not controlled through the display terminal. However, in other embodiments the display terminal may be used for opening the dispensers and electronic lock drawers for restocking purposes as well. Once the user restocking the items has completed the information associated with the restocking activity, they can log out of the display terminal by selecting button 232.

Retrieve button 294 is likewise used by a selected group of authorized users. The retrieve button is used to enable certain selected users who have authority to access medications that have been returned or wasted and which are stored in a particular retrieve drawer. Such an authorized user has an associated record in the data store that authorizes them to do this and when such a user authorizes the system and selects this button, the retrieve drawers may be opened. To enable the user to retrieve such items, the process of retrieving returned or wasted medications is described in copending U.S. application Ser. No. 08/679,203 filed Jul. 12, 1996, the disclosure of which is incorporated herein by reference. Again, after a user has conducted a retrieve activity, they may exit from the system by selecting the log-out button 232.

The medication dispensing system of the present invention may be used in connection with a plurality of different types of devices which store and dispense medical items. For purposes of narcotics, which are tightly controlled, a medicine dispenser which holds the medical items in a secure enclosure prior to dispense and which dispenses such items in a manner that can be controlled and confirmed is preferred. Medicine dispenser 100 is such a dispenser that is used in connection with dispensing medications in a preferred embodiment of the invention.

Figure 23:
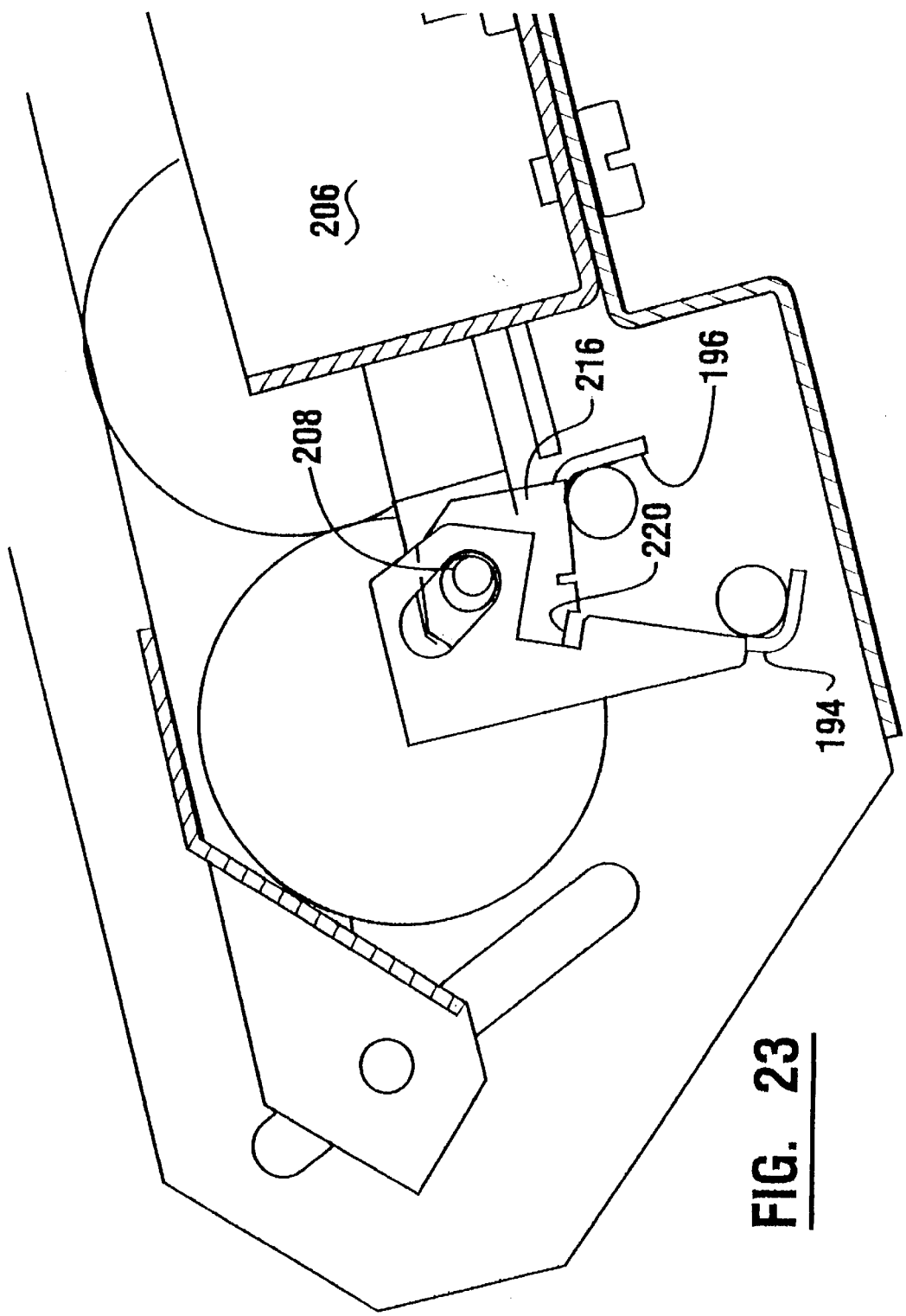
FIG. 23 is a side view of the dispenser mechanism with the gate members in the positions shown in FIG. 16.
Figure 24:
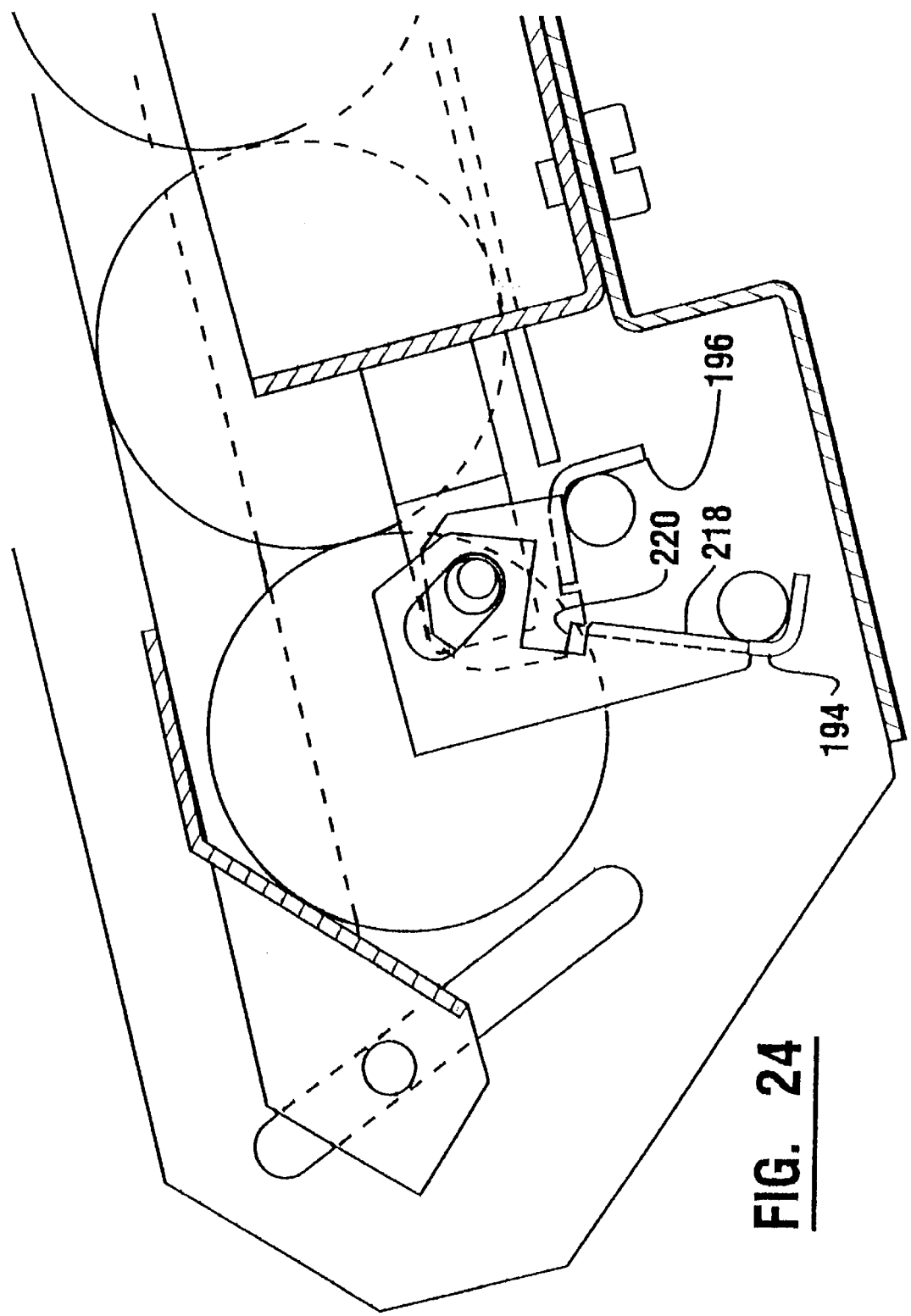
FIG. 24 is a side view of the dispenser mechanism corresponding to FIG. 23 including hidden edge lines.
Figure 25:
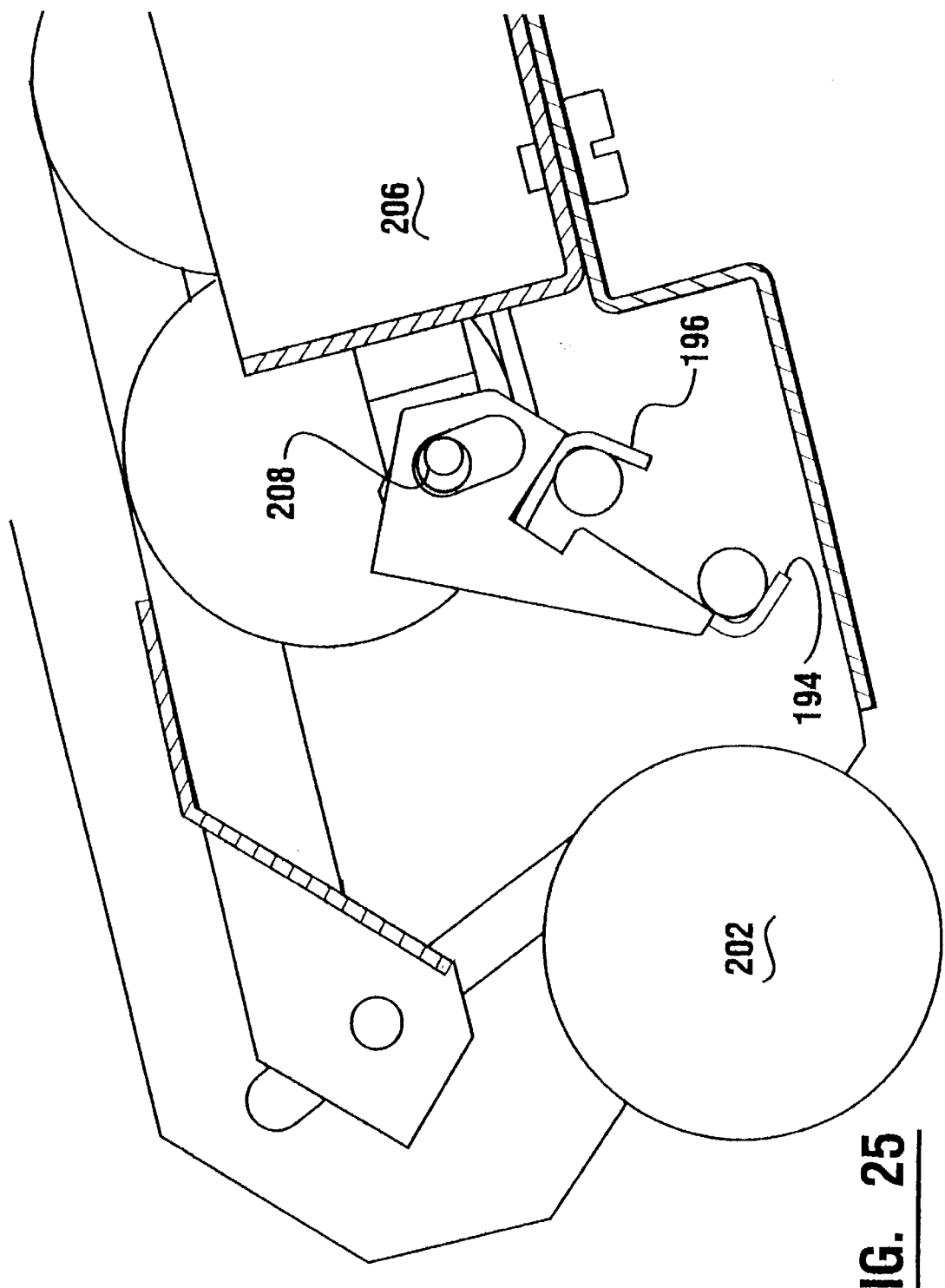
FIG. 25 is a side view of the dispenser mechanism with the gate members in the positions shown in FIG. 17.
Figure 26:
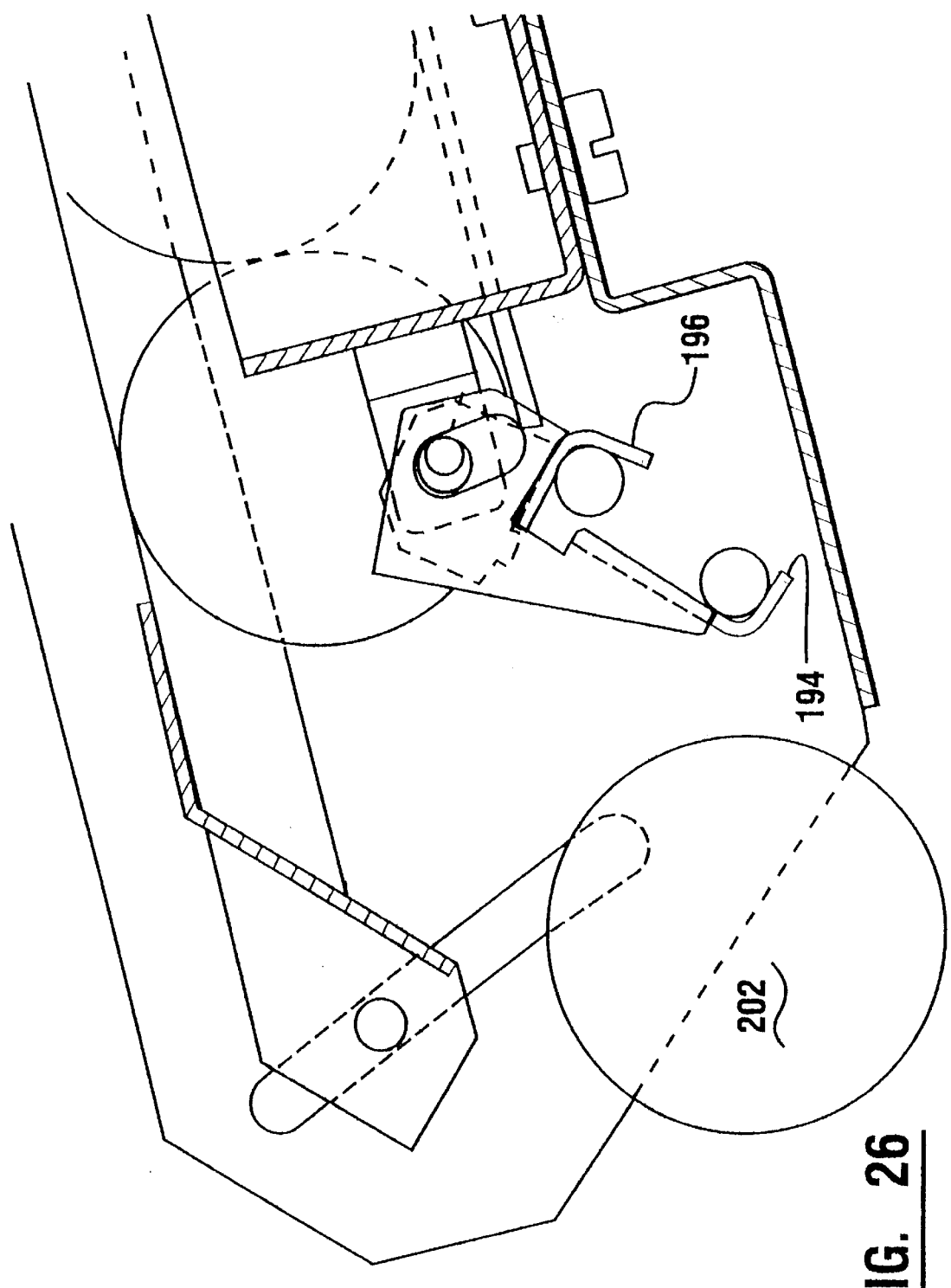
FIG. 26 is a side view of the dispenser mechanism corresponding to FIG. 25 including hidden edge lines.
Figure 27:
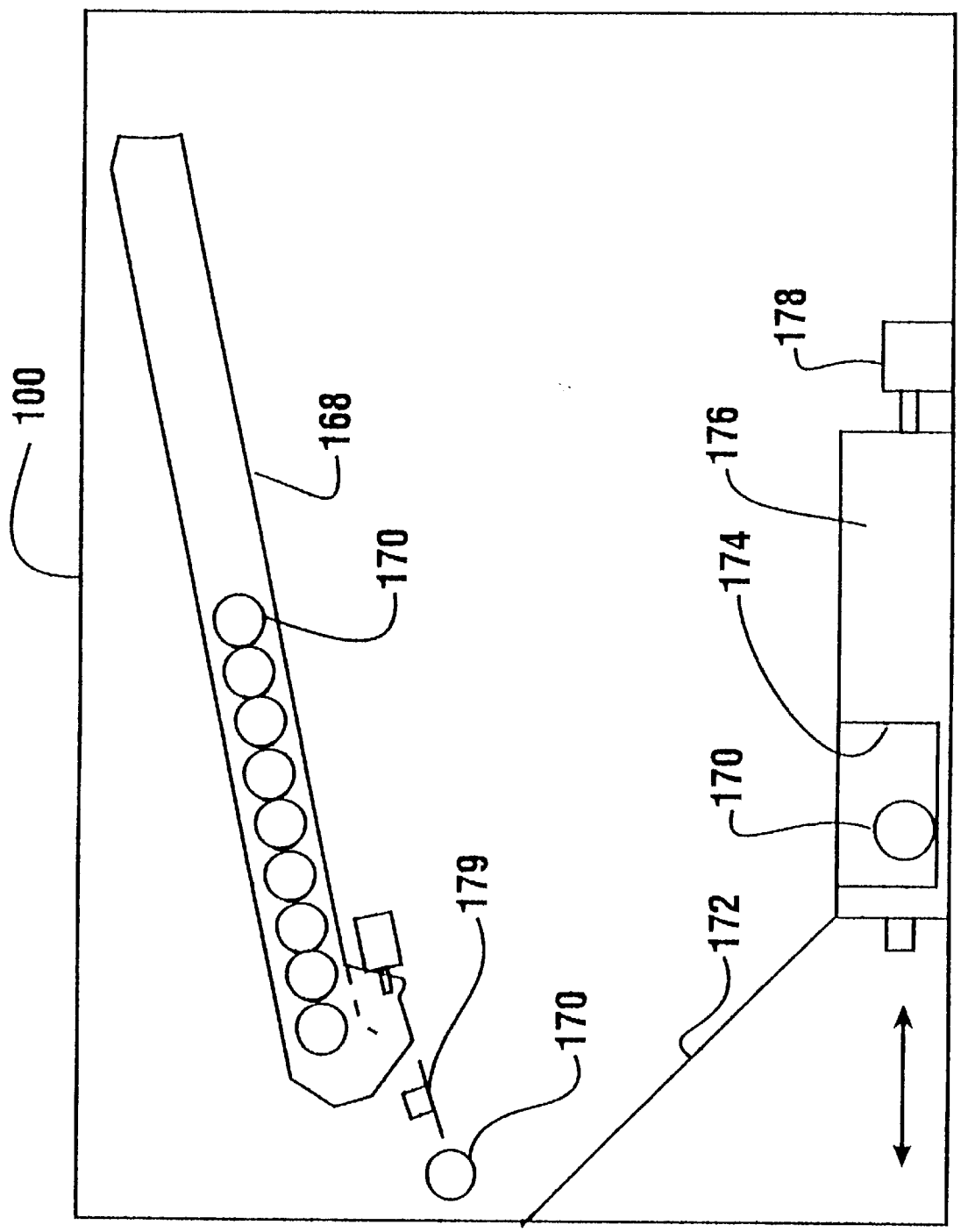
FIG. 27 is a sectional side view of the dispenser mechanism shown in FIG. 14 located inside a medicine dispenser.

The interior of medicine dispenser 100 is shown schematically in FIG. 23. Dispenser 100 encloses a plurality of dispenser magazines 168 only one of which is shown. Each magazine holds a plurality of ampules, vials or other medication holding containers 170 which are held in inclined relation in the magazine. Each of the containers in a particular magazine contains a predetermined dose of a substance such as a narcotic material that may be prescribed to a patient. Many forms of cylindrically packaged medications or medical items may be held in the magazines. Medicine dispenser 100 optimally houses a large number of magazines, each one holding vials with a particular type of medicine. Each magazine 168 includes a dispensing mechanism later described in detail that releases containers in response to electrical signals one at a time from the lower end of the magazine. Released vials are guided on a chute 172 into a pocket 174 in a drawer 176. Drawer 176 may be a simple drawer or in alternative embodiments may be controllably locked and unlocked by an electronic lock 178 shown schematically inside the medicine dispenser. Each magazine has a dispense verification sensor 179 associated therewith. Sensor 179 is operable to detect the actual dispense of a container from a magazine. Sensor 179 may be an optical, mechanical or other suitable sensor type.

When medicines are requested at the display terminal 102, the appropriate containers from the magazines 168 are released and fall down the chute into the pocket 174. After the vials have been released and are in position in the pocket, they may be taken. In alternative embodiments in which the drawer is controlled, the data terminal 102, in response to signals from the computer 84 unlocks the electronic lock 178 and enables the drawer 176 to be pulled outwardly so that the containers in the pocket may be taken.

Replenishment of the medicine dispenser 100 is accomplished by manually replenishing the magazines and indicating that fact through the data terminal in the manner previously described. To accomplish this the medicine dispenser has to be opened. This is possible only under the most secure of circumstances and through the use of a mechanical locking system comparable to that which is conventionally used to secure narcotics. Normally, two keys are required to open the unit and each key is in the possession of a different person.

Figure 10:
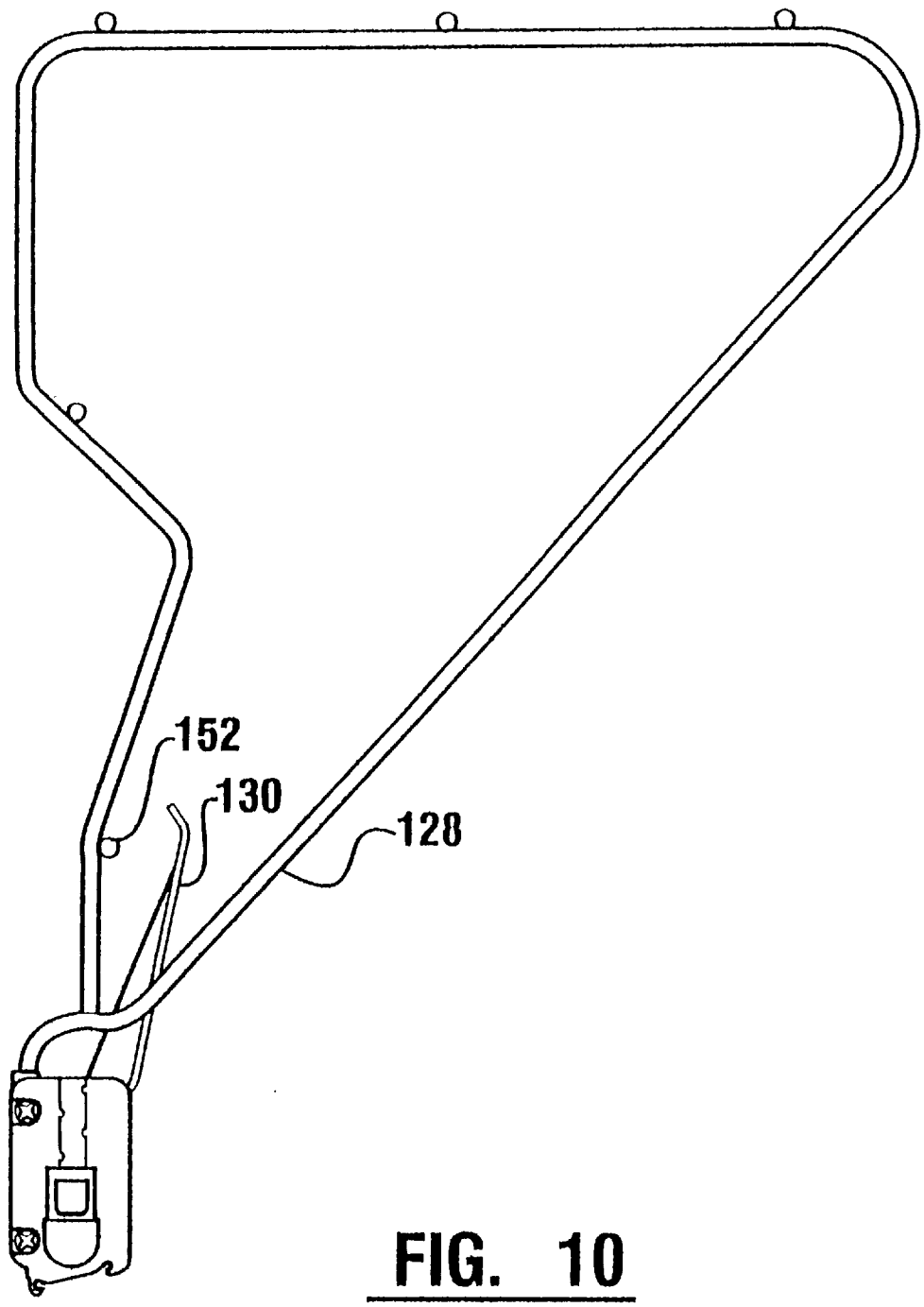
FIG. 10 is a partial side view of the box register along line 10—10 in FIG. 9.
Figure 11:
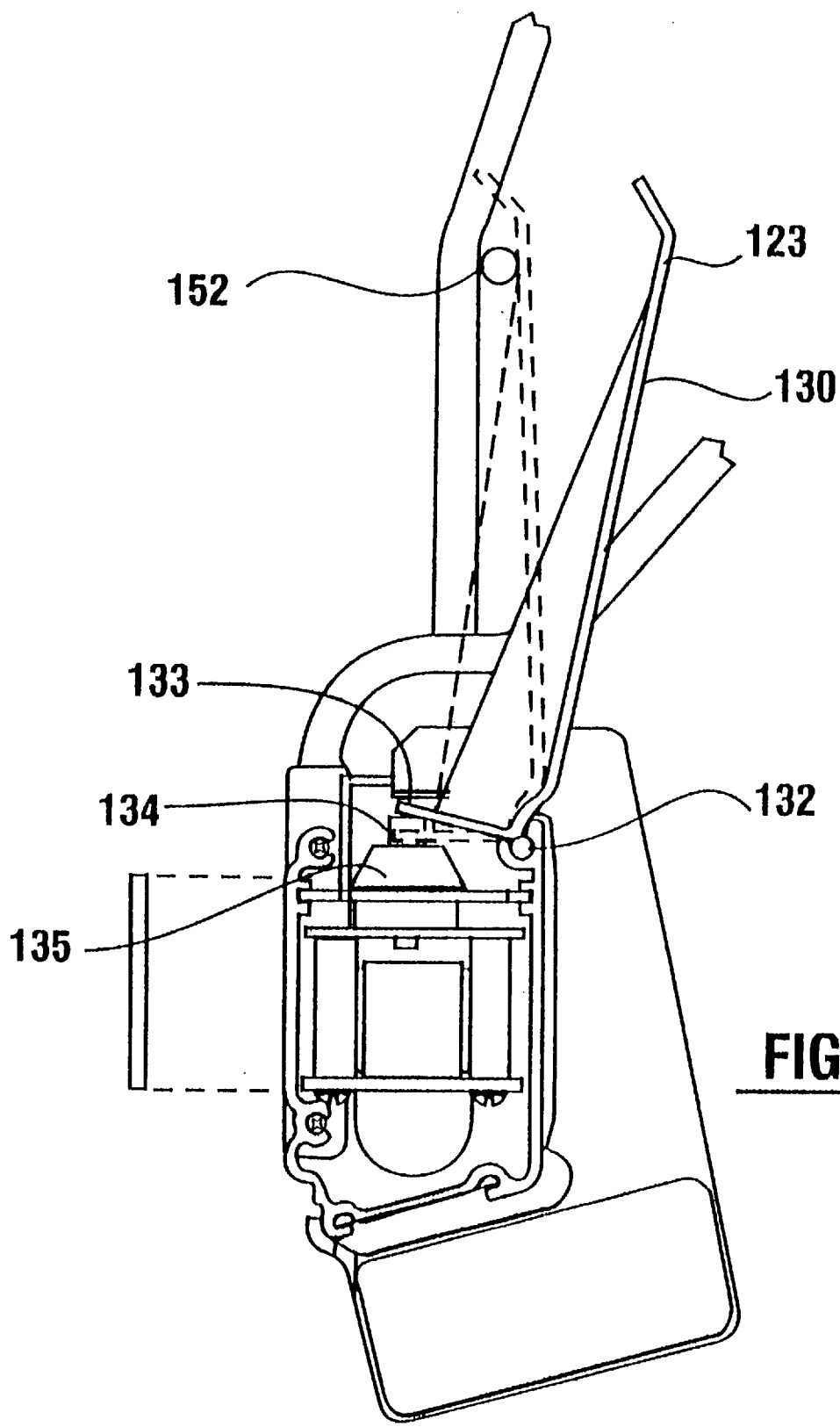
FIG. 11 is an enlarged side view of a switch and lever of the box register shown in FIG. 9.
Figure 12:
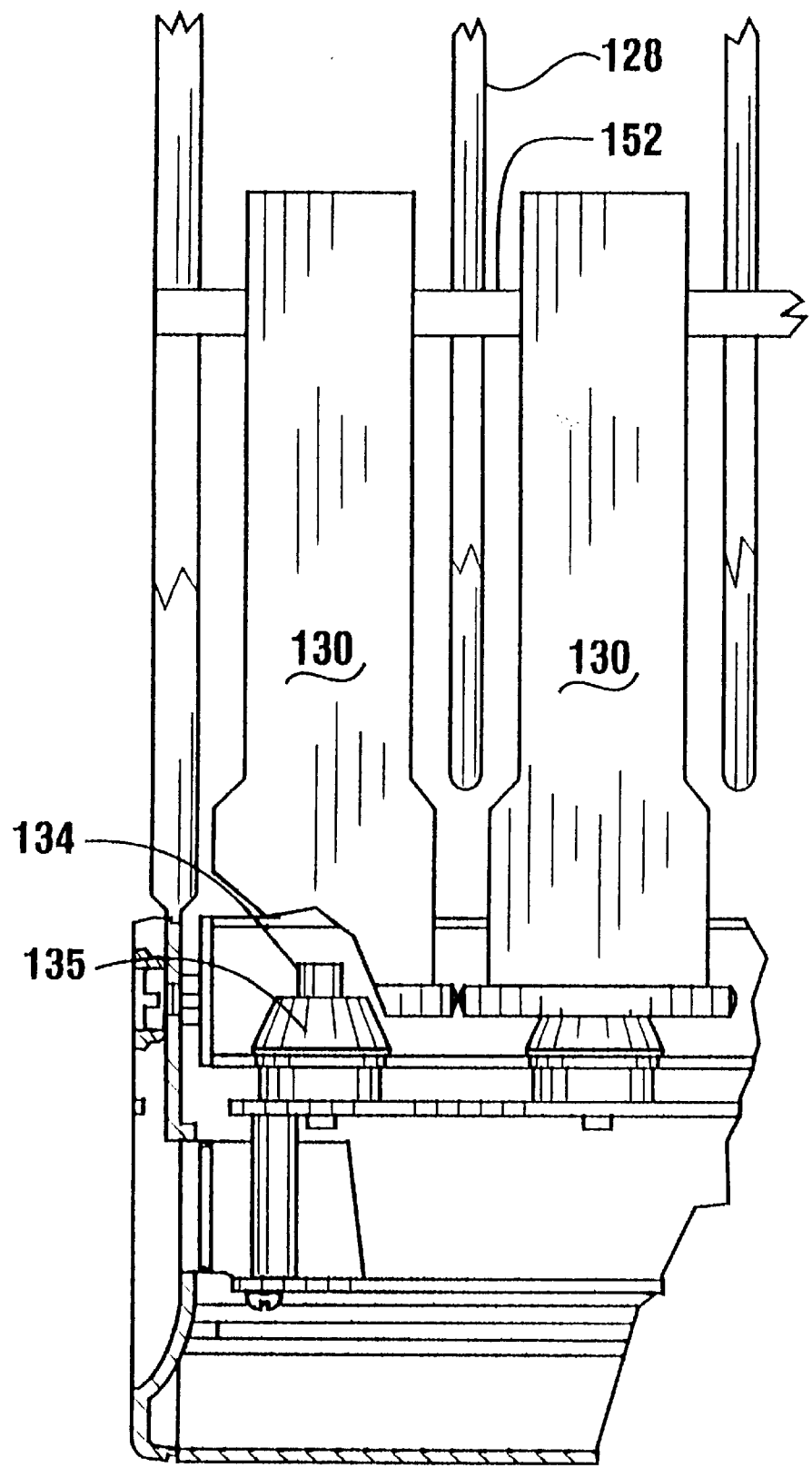
FIG. 12 is a front, partial cut away view of the lever and switch of the box register shown in FIG. 9.
Figure 13:
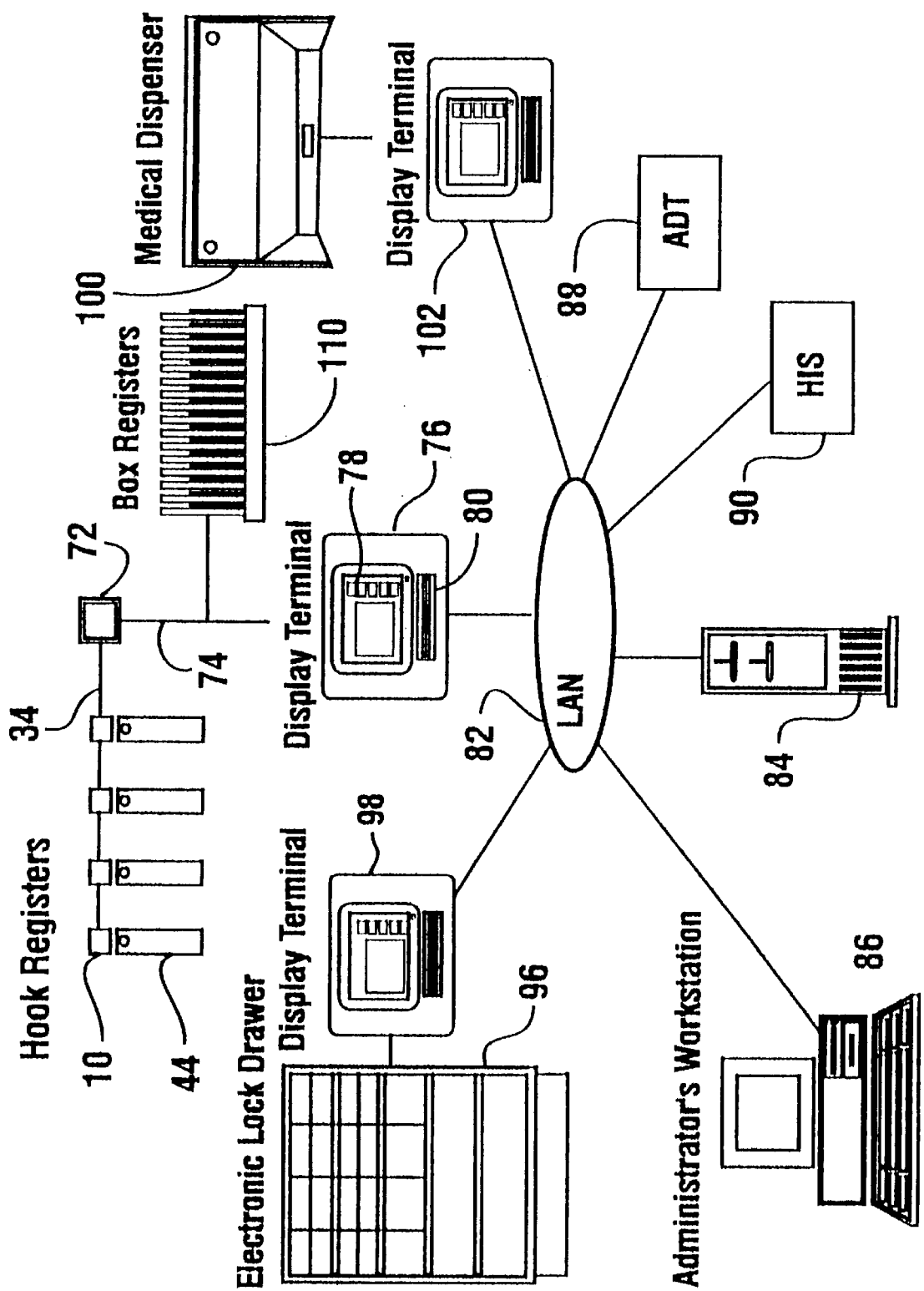
FIG. 13 is a schematic view of the system for monitoring and dispensing medical items including the hook registers and box registers.

The operation of the dispensing mechanism is shown in greater detail in FIGS. 10 through 22. FIG. 10 shows the vials or other containers 170 in the magazine 168. As shown in FIGS. 11 through 13 because the magazine is tilted downward the containers tend to roll towards the front of the magazine toward an opening 180. The container adjacent the opening 180 contacts a guide 182 which is dog-legged in cross section. Guide 182 includes a tapered face 184 which is engaged by the first container 202 in the magazine. Guide 182 further includes an arm portion 186 that extends longitudinally adjacent the vials. Arm portion 186 has attached adjusting pins 188 which extend through the side walls 190 of the magazine. Adjusting pins 188 extend in angled slots 192 and may be fixed at selected positions therein using nuts mounted on the pins or other suitable locking fasteners.

The movable mounting of the guide 182 enables the magazine to accommodate different diameter containers by moving the guide in the slots 192 to provide sufficient clearance for a container to pass onto the guide adjacent opening 180 but not so much clearance so that the vial can fall out the opening without the actuation of the gate members as later explained.

Figure 14:
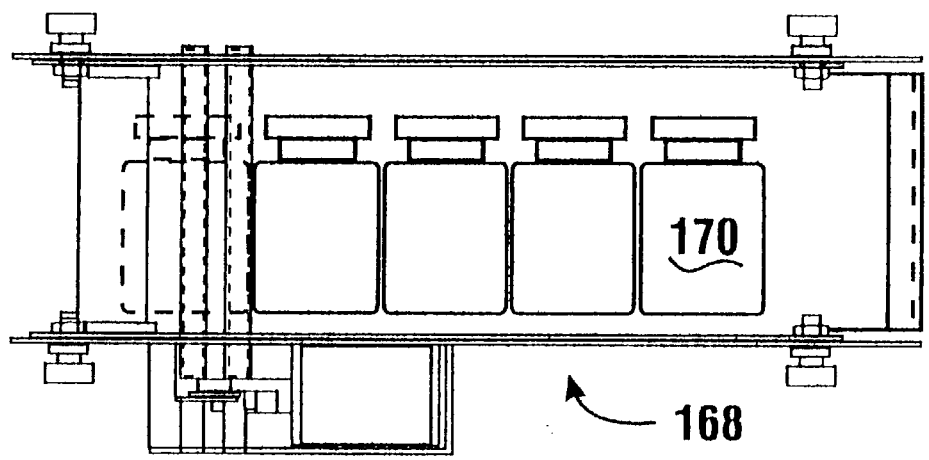
FIG. 14 is a top plan view of a dispenser mechanism for vials containing medications.
Figure 15:
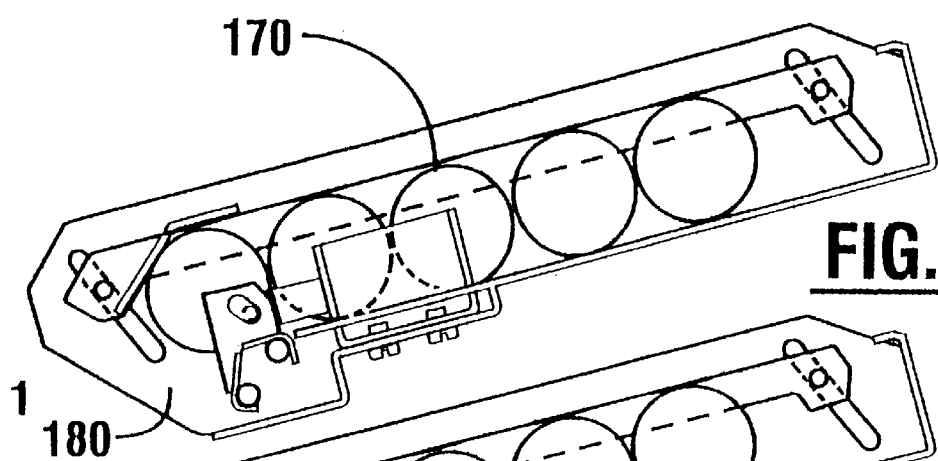
FIG. 15 is a cut-away side view of the dispenser shown in FIG. 14 with the gate members thereof in a first position.
Figure 16:
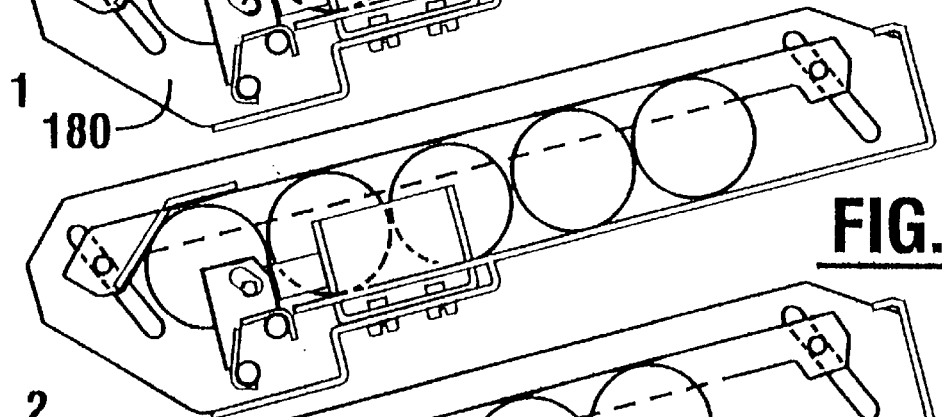
FIG. 16 is a view similar to FIG. 15 with the gate members of the dispenser in a second position.

As best shown in FIGS. 14 through 16, a front gate 194 and a back gate 196 are mounted adjacent to opening 180. The front gate and back gate are mounted on a front gate shaft and a back gate shaft 198 and 200 respectively.

As shown in FIG. 14 in the inoperative position of the gate members front gate 194 engages the underside of first vial 202 adjacent opening 180. The end of front gate 94 engages container 202 at a position outward towards opening 180 from a location on the surface of the container diametrically opposite where container 202 engages tapered face 184 of guide 182. As a result, the container 202 is prevented from passing out through opening 180. In this position any force applied to 202 (if it could be accessed) would tend to be resisted by compressive forces making it very difficult for the container to be manually removed. In the inoperative position of the magazine shown in FIG. 14 the back gate 196 has its upper end extending parallel to a bottom wall 204 of the magazine. As a result, in this position the back gate does not interfere with movement of the containers.

In the actuation sequence for dispensing a container, the back gate rotates in a clockwise direction to the position shown in FIG. 15. As it does this the back gate begins to move to a position blocking the container immediately behind container 202 in the magazine from moving toward the opening 180. In the position shown in FIG. 15 the front gate 194 remains in its original blocking position holding container 202 in the magazine.

After the back gate has begun to rise as shown in FIG. 15, the front gate begins to rotate in a clockwise direction toward the position shown in FIG. 16. As the front gate 194 rotates container 202 is no longer held in the magazine and passes out the opening 180. The back gate having fully rotated as shown in FIG. 16, holds the next container in the magazine from moving until the front gate returns to its original position shown in FIG. 14. When this occurs the back gate returns to its original position allowing the containers to roll forward and the next container is now in the position of container 202.

In the preferred embodiment of the invention, the slots 192 are oriented such that for any size container reasonably accommodated in the magazine, the front and back gates are positioned so that the front gate 194 may assume an overcenter blocking position in the closed position and the back gate can move to prevent the dispense of more than one container at a time. This ensures that with each cycle of the front and back gates only one container is dispensed.

Figure 17:
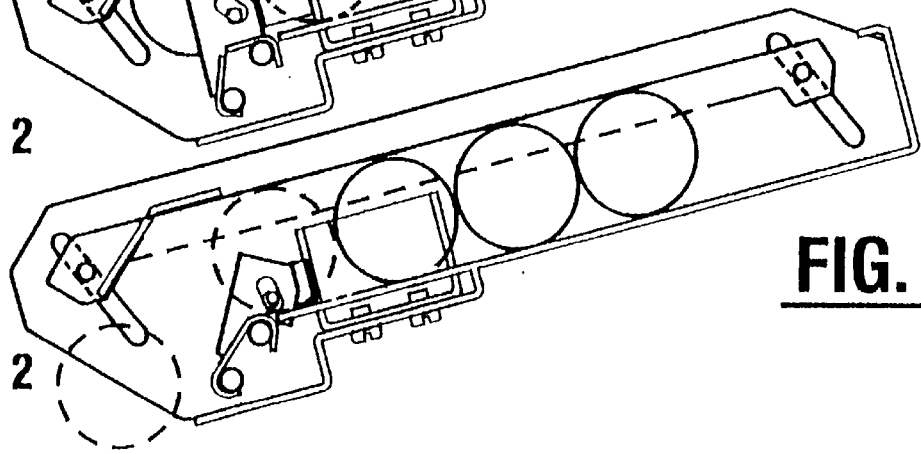
FIG. 17 is a side view similar to FIG. 16 with the gate members in a third position wherein a vial is dispensed from the mechanism.
Figure 18:
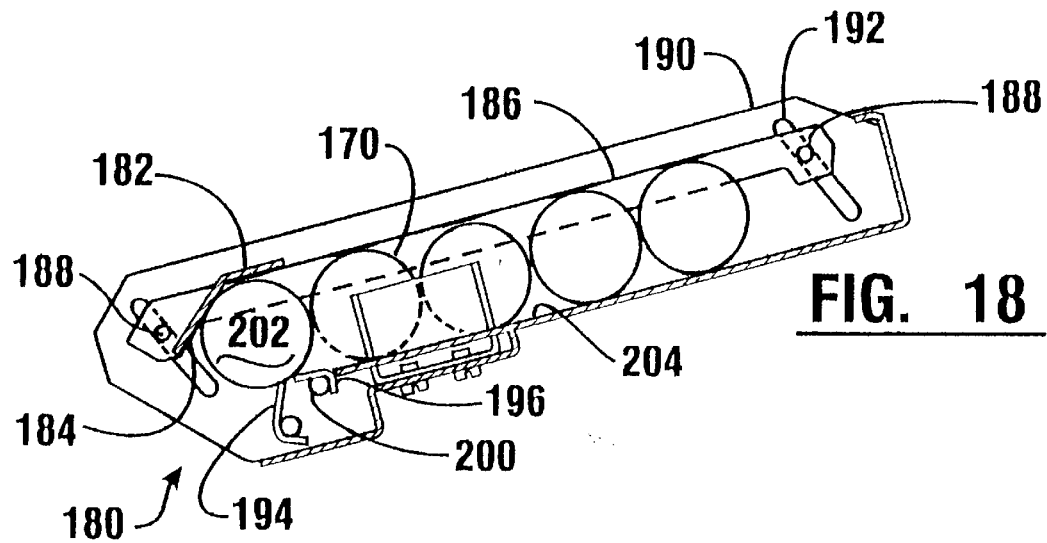
FIG. 18 is a cross sectional view corresponding to the dispenser as shown in FIG. 15.

The actuating mechanism for the front and back gates is shown in FIGS. 17 through 22. As shown in FIG. 17 the actuating mechanism for the gates includes an electrical solenoid 206. Solenoid 206 has an actuating plunger member with a pin 208 extending traversely therefrom. Pin 208 extends traversely in a first slot 210 in a first actuator plate 212 which is attached to the front gate 194. Pin 208 also extends through an opening 214 in a second actuator plate 216 which is attached to back gate 196. As best shown in FIG. 18 first actuator plate 212 has a traversely extending finger 218. In the position of the front gate shown in FIGS. 17 and 18, finger 218 engages a detent 220 in the second actuator plate 216. The purpose of detent 220 is to prevent finger 218 and front gate 212 from moving in a clockwise direction whenever the second actuator plate 216 is in its inoperative position as shown in FIGS. 17 and 18. This prevents a person who may gain access to the front of the magazine from being able to deflect the front gate so as to cause the containers to be removed from the magazine.

Figure 19:
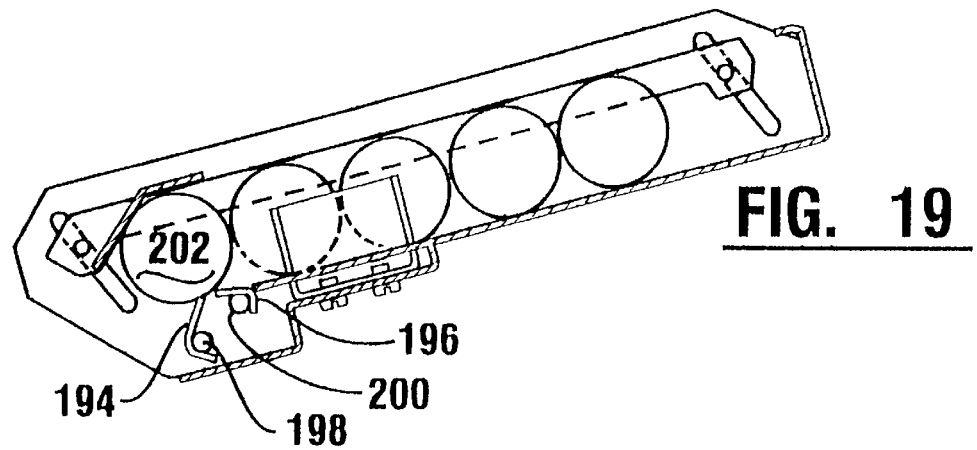
FIG. 19 is a side view of the dispenser mechanism corresponding to FIG. 16.
Figure 20:
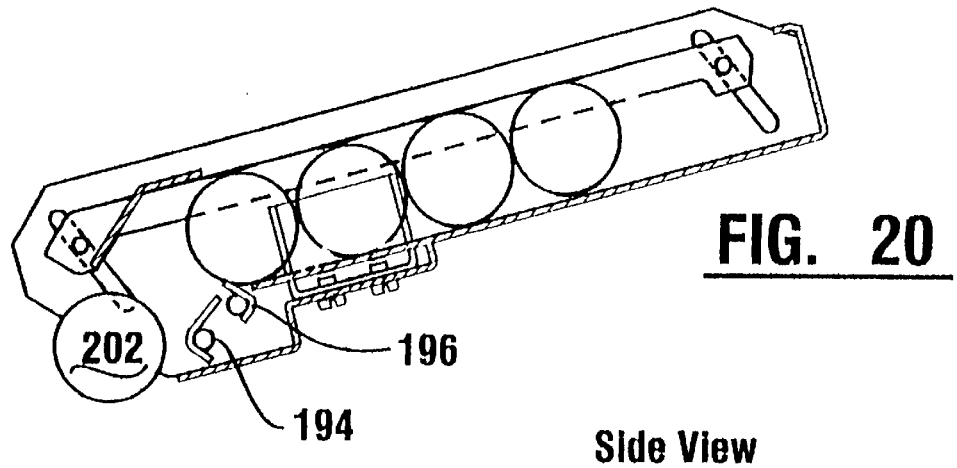
FIG. 20 is a side view of the dispenser mechanism corresponding to FIG. 17.
Figure 21:
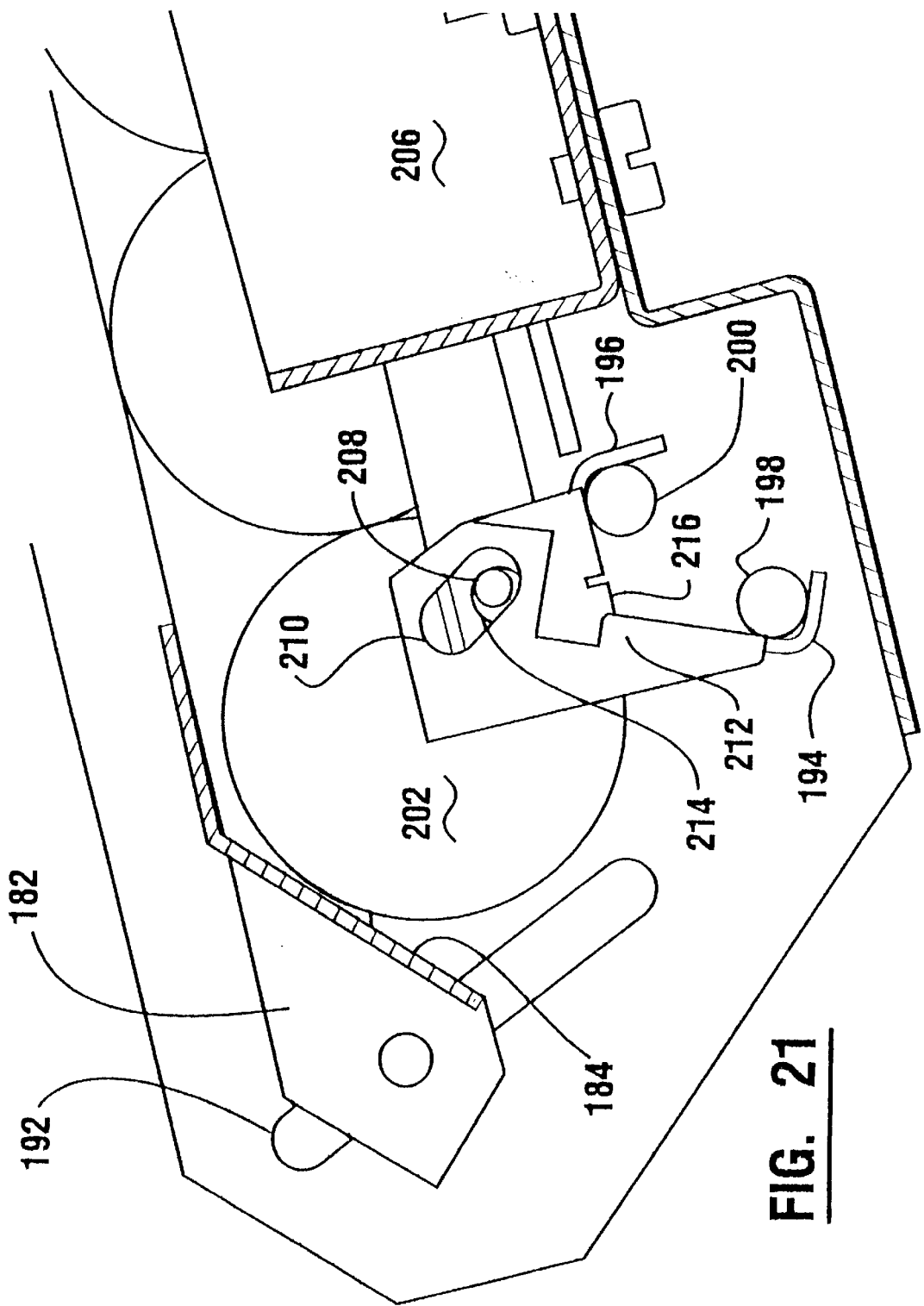
FIG. 21 is a side view of the dispenser mechanism and gate members in the positions shown in FIG. 15.
Figure 22:
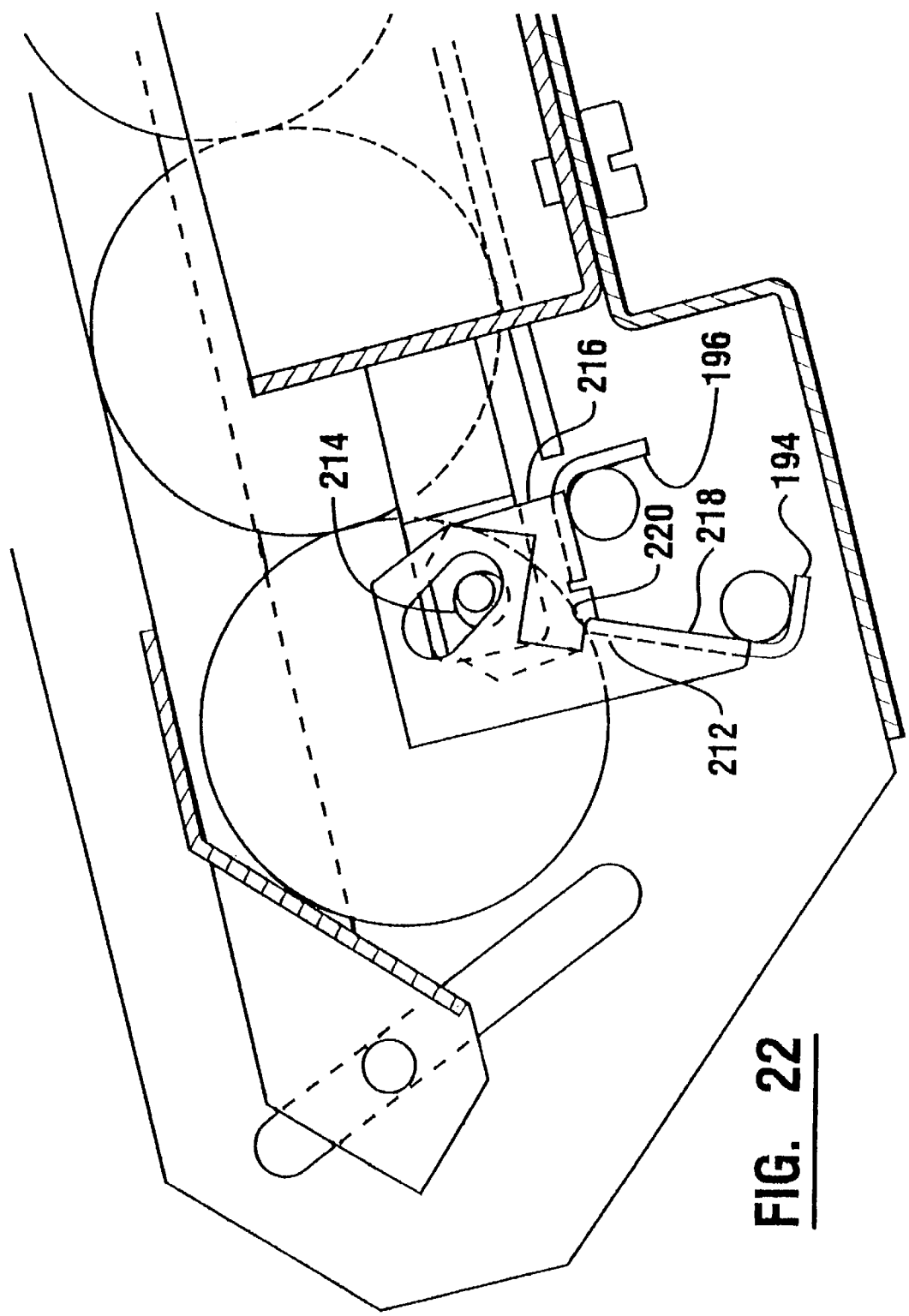
FIG. 22 is a side view corresponding to FIG. 21 including hidden edge lines.

As shown in FIGS. 19 and 20 the actuation of solenoid 206 by an electrical signal from the data terminal causes pin 208 to move second actuator plate 216 in a clockwise direction. This causes back gate 196 to move upward and detent 220 to disengage from finger 218. As a result, front gate 194 may move only after back gate 196 has risen so as to block the dispense of further containers. Upon further movement of pin 208 by solenoid 206 the front and back gate move to the positions shown in FIGS. 21 and 22. In these positions the front gate is rotated so as to release container 202 while the back gate is extended fully upward so as to prevent the discharge of the next container in the magazine. Thereafter, discontinuance of the electrical signal to solenoid 206 returns the gate members to their original positions and allows the next container to assume the position adjacent to the opening from the magazine.

The dispensing mechanism of the present invention enables the controlled dispense of one container at a time from the magazine in response to an electrical signal. This assures that only the requested medication is dispensed. The same magazine may be readily adapted to containers or items of varying diameter by adjusting the position of guide 182. The magazine also accommodates containers of different lengths. In addition, the gate members are suitably secure so as to avoid tampering by persons who might attempt to gain access to the interior of the medicine dispenser 100 through the dispenser drawer 176.

The dispensing mechanism also assures that the requested medical item has been dispensed. This is assured by using signals generated by sensor 179 to minimize the risk that a dispense will be recorded which has not actually occurred due to a malfunction. Circuitry in the dispenser is connected to the sensor 179 and transmits signals when a container passes out of a magazine. These signals are checked to see if they are generated when a signal to dispense to the corresponding magazine is given. The dispense of any item from a location and the provision of such item to a patient is only recorded in the computer data store when the dispense is verified by the sensor associated with the magazine. Alternatively, in other embodiments a bar code reader may be installed in the dispenser and bar code applied to the containers to verify not only the dispense but the type of item dispensed.

Although in the above described embodiment of the medicine dispenser the gate members are shown as extending the entire width of the magazine, in other embodiments the gate members may have other configurations and may be of different designs so as to extend only a portion of the width. Although in the preferred form of the invention the magazines extend in downward tilted relation in other embodiments they may be arranged to extend vertically. In such alternative embodiments guides may be provided to hold the containers adjacent to plate 204. Further, the containers may be dispensed in a vertically upward direction through incorporation of spring loading to bias the containers upward in the magazine. A fundamental aspect of the invention is that the gate member which corresponds to the front gate member engages the container in an over-center position with regard to where the container contacts the tapered face, and the back gate member moves in synchronized relation with the front gate member to prevent the dispense of more than one container at a time.

The system for monitoring and dispensing medical items which includes the hook registers, box registers, electronic lock drawer and medicine dispenser previously described may also include or be used with other types of devices. These may include automatic dispensing devices as well as manual devices for which the inventory and use information can be input as a matter of practice at a conveniently located data terminal. The system of the present invention is highly adaptable to accommodate medical facilities of varying size. As the system of the present invention is also connected to a variety of computers which include data stores, a wide variety of parameters may be monitored and evaluated so as to avoid conditions of waste, fraud and abuse.

Thus the new system for dispensing and monitoring medical items of the present invention achieves the above stated objectives, eliminates difficulties encountered in the use of prior systems, solves problems and attains the desirable results described herein.

In the foregoing description certain terms have been used for brevity, clarity and understanding. However, no unnecessary limitations are to be implied therefrom because such terms are for descriptive purposes and are intended to be broadly construed. Moreover, the descriptions and illustrations given are by way of examples and the invention is not limited to the exact details shown or described. In addition, any feature of the invention that is described in the following claims as a means for performing a function shall be construed as encompassing any means capable of performing the recited function and shall not be limited to the means disclosed in the foregoing description or any mere equivalent thereof.

Having described the features, discoveries and principles of the invention, the manner in which it is constructed and utilized, and the advantages and useful results obtained, the new and useful structures, devices, elements, arrangements, parts, combinations, systems, equipment, operations, methods and relationships are set forth in the appended claims.

We claim:

1. A system for providing medical items comprising:
    a dispenser, wherein said dispenser is selectively operative to dispense a of a plurality of medical items stored in the dispenser;
    a user terminal, wherein said user terminal includes a display and an input device, wherein said dispenser is in operative connection with said user terminal and said dispenser is operative to dispense medical items responsive to said user terminal;
    a data store in operative connection with said user terminal, wherein said data store includes kit data representative of a kit, wherein said kit data comprises data representative of multiple medical items, which items are to be used in a future medical procedure;
    wherein said multiple medical items included in said kit are dispensed by said dispenser responsive to an input to said input device of said user terminal.

2. The system according to claim 1 wherein said data store includes kit data representative of a plurality of different kits, wherein each kit comprises multiple medical items to be used in a different future medical procedure, and wherein said display of said user terminal is operative responsive to said input device to display data identifying each of said plurality of kits, and wherein said input device is operable to select identifying data associated with one of said plurality of said kits, and wherein said dispenser is operative to dispense the multiple medical items included in the one selected kit responsive to said selection of said identifying data associated with said one kit.

3. The system according to claim 1 wherein said data store further comprises patient data representative of a patient, and wherein said kit data is stored in correlated relation with said patient data, whereby said kit data corresponds to a medical procedure scheduled for the patient.

4. The system according to claim 3 wherein the input device is selectively operative to cause said display of said user terminal to display data representative of a patient with data identifying a kit associated with a procedure scheduled for said patient.

5. The system according to claim 4 wherein said patient data includes data representative of medical items taken from the system for use by said patient, and wherein said input to the input device is operative to cause to be included in said data store, data indicative that the multiple items included in said kit have been taken for use by the patient.

6. The system according to claim 5 wherein said data store includes data representative of pricing information for said medical items, and wherein said input device is operative to include in correlated relation with said patient data, data indicative of the price of at least one of the dispensed items included in the kit.

7. The system according to claim 1 wherein said data store further comprises data representative of a brand name and a generic name for at least one of said medical items included in said kit, and wherein said user terminal is operative responsive to said input device to display on said display of said user terminal item data representative of each of the items included in said kit, wherein said item data includes one of either the brand name or generic name for said one item in said kit, and wherein said input device includes a selector, wherein said selector is operative when selected to change said displayed one item data to said other of said generic name or brand name.

8. The system according to claim 1 wherein said data store includes data representative of a plurality of said kits and a designator for each of said plurality of said kits, wherein said input device is operative to selectively display said designators associated with more than one of said kits on said display of said user terminal, and wherein said input device is operable to select one of said designators, and wherein said dispenser is operative responsive to selection of said one selected designator to dispense the multiple items included in a selected kit associated with said one selected designator.

9. A system according to claim 8 wherein said input device includes a touch screen, and wherein said input device further includes a button on a window displayed on said touch screen, wherein selecting said button is operative to cause said items included in the selected kit to be dispensed by said dispenser.

10. The system according to claim 1 wherein said kit comprises at least one medical item not dispensable from said dispenser, and wherein said display is operative responsive to the input to the input device to prompt on said display of said user terminal for a user to take said one item from a location external to said dispenser.

11. A system for providing medical items comprising:
a data store wherein said data in said data store includes data representative of a kit, wherein said kit comprises multiple medical items expected to be used in the course of a future medical procedure;
a user terminal in operative connection with said data store wherein said user terminal includes a display and an input device;
wherein said user terminal is operative responsive to said input device to display kit identification data representative of said kit on said display, and wherein data indicative that said multiple medical items included in said kit have been taken by a user is included in the data store in response to an input to the input device.

12. The system according to claim 11 wherein said data store further comprises patient identification data representative of the identities of a plurality of patients, and wherein said user terminal is operative responsive to said input device to select patient identification data associated with one of said patients, and wherein responsive to said input to the input device said data representative of the multiple medical items comprising the kit are stored in the data store in correlated relation with the patient data corresponding to said one selected patient.

13. The system according to claim 12 wherein said input device includes a touch screen on said user terminal, and wherein said input device further includes a window presented on said touch screen including said patient identification data or said kit identification data, and wherein said input device includes a highlighting device for highlighting at least one of said patient identification data or said kit identification data in said window responsive to a touch by a user of said data on said window.

14. A system for providing medical items comprising:
a dispenser, wherein said dispenser is selectively operable to dispense any of a plurality of medical items stored therein;
a user interface, wherein said user interface includes a display and an input device, wherein said dispenser is in operative connection with said user interface and said dispenser is operative to dispense selected medical items responsive to said user interface;
a data store in operative connection with said user interface, wherein said data store includes kit data representative of a kit, wherein said kit comprises multiple medical items which items are expected to be used in a future medical procedure;
wherein multiple items included in said kit are dispensed by said dispenser responsive to an input corresponding to the kit being input to the input device of said user interface.

15. A method for providing medical items comprising the steps of:
storing in a data store item data representative of multiple medical items in at least one kit, wherein said multiple medical items in said kit are items to be used in the course of a future medical procedure; displaying on a display of a user terminal responsive to an input to an input device, item-identifying data representative of the multiple medical items included in said kit.

16. The method according to claim 15 wherein said storing step further comprises storing in said data store kit data representative of data identifying said kit, and wherein said displaying step comprises selectively displaying responsive to said input device either said item-identifying data or said kit-identifying data.

17. The method according to claim 16 and further comprising the steps of:
selecting with said input device said displayed kit-identifying data associated with said kit, and
dispensing at least one of said medical items in said kit from a dispenser responsive to said selection of said kit-identifying data.

18. The method according to claim 15 wherein said medical procedure comprises a medical procedure for a specific patient.

19. The method according to claim 15 wherein said medical procedure comprises a standardized medical procedure suitable for use in connection with a plurality of patients.

20. The method according to claim 16 wherein said storing step further comprises storing in said data store patient data representative of an identity of a patient, and wherein said medical procedure is associated with said patient, and wherein said kit data is stored in correlated relation with said patient data, and wherein in said displaying step indicia corresponding to said patient identity is displayed on said display of said user terminal with said kit-identifying data.

21. A method for providing medical items comprising the steps of:
storing in a data store patient data representative of identities of a first plurality of patients, and kit data representative of a second plurality of medical kits, wherein each of said kit includes at least two (2) medical items, wherein the items included in one kit are items to be used in the course of a future medical procedure;
selecting a patient using an input device at a user terminal;
selecting the one kit using the input device of the user term;
indicating by using said input device of said user term that the medical items included in the one kit have been taken for the selected patient.

22. A system for providing medical items comprising:
a dispenser, wherein the dispenser includes a plurality of storage locations and is operative to selectively dispense any of a plurality of different types of medical items stored in the storage locations, wherein different types of medical items are stored in different storage locations in the dispenser prior to dispense;

a data store in operative connection with a user terminal, wherein the data store includes kit data representative of a kit, wherein the kit includes at least two different types of medical items to be used in the conduct of one future medical procedure;

wherein the medical items comprising the kit are dispensed from the storage locations by the dispenser responsive to a single manual input to the input device of the user terminal.

23. A system for providing medical items comprising:

a dispenser, wherein the dispenser is selectively operative to dispense any of a plurality of medical items stored in the dispenser;

a user interface, wherein the user interface includes an input device, wherein the dispenser is in operative connection with the input device and the dispenser is operative to dispense medical items responsive to inputs to the input device;

a data store in operative connection with the user interface, wherein the data store includes kit data representative of a kit, wherein the kit data includes data representative of multiple medical items to be on hand during the course of performing a future medical procedure; and wherein multiple medical items included in a kit are dispensed by the dispenser responsive to an input to the input device.

24. A method comprising the steps of:

placing a plurality of medical items in a dispenser, wherein the dispenser has a plurality of storage locations and wherein different types of medical items are stored in different storage locations prior to dispense from the dispenser;

storing in a data store data representative of a kit, wherein the kit data includes data representative of one future medical procedure and at least two different types of medical items desirable to have available for use while performing the one medical procedure;

receiving a single manual input through an input device, the input corresponding to the medical procedure, wherein the input device is in operative connection with the dispenser;

dispensing the two different types of medical items included in the kit from their respective storage locations in the dispenser in response to the manual input.

25. The method according to claim 24 and prior to the receiving step, further comprising the step of displaying indicia representative of the medical procedure on a display.

26. The method according to claim 24 and further comprising prior to the receiving step, the steps of:

further storing in the data store data representative of a plurality of different patients; and selecting a particular patient with a selecting device;

and after the dispensing step further comprising the step of:

storing in the data store data representative of the two different types of dispensed medical items in correlated relation with the data representative of the particular patient.

27. The system according to claim 14 wherein the data store further includes data representative of a plurality of patients and at least one future medical procedure scheduled for each of the patients, and wherein the kit data includes for each future medical procedure data corresponding to multiple medical items to be used in the procedure, and wherein indicia representative of a patient and a kit corresponding to the medical procedure scheduled for the patient are displayed together on the display of the interface.

28. The system according to claim 14 wherein the future medical procedure is a surgical procedure.

29. The system according to claim 14 wherein the future medical procedure is a diagnostic procedure.

* * * * *

UNITED STATES PATENT AND TRADEMARK OFFICE
CERTIFICATE OF CORRECTION

PATENT NO.  : 5,848,593
DATED       : December 15, 1998
INVENTOR(S) : R. Michael McGrady, et al.

It is certified that error appears in the above-identified patent and that said Letters Patent is hereby corrected as shown below:

Column 32, lines 56-57, "user term" is changed to
-- user terminal --.

Column 32, line 58, "user term" is changed to -- user terminal --.

Signed and Sealed this

Twentieth Day of April, 1999

Attest:

Q. TODD DICKINSON

*Attesting Officer*          Acting Commissioner of Patents and Trademarks